(12) United States Patent
Wild

(10) Patent No.: US 6,607,542 B1
(45) Date of Patent: Aug. 19, 2003

(54) SURGICAL APPARATUS AND METHOD FOR OCCLUDING OR ENCIRCLING A BODY PASSAGEWAY

(76) Inventor: Andrew Michael Wild, P.O. Box 253, Reigate, Surrey (GB), RH2 9FJ ( * ) Notice: Subject to any disclaimer, the term of this patent is extended or adjusted under 35 U.S.C. 154(b) by 0 days.

(21) Appl. No.: 09/857,874

(22) PCT Filed: Dec. 10, 1999

(86) PCT No.: PCT/GB99/04164

§ 371 (c)(1),
(2), (4) Date: Jul. 17, 2001

(87) PCT Pub. No.: WO00/35355

PCT Pub. Date: Jun. 22, 2000

(30) Foreign Application Priority Data

Dec. 11, 1998 (GB) .............................. 9827415

(51) Int. Cl.[7] .............................. A61B 17/08
(52) U.S. Cl. .................. 606/157; 606/139; 606/142; 606/158
(58) Field of Search ................ 606/157, 158, 606/139, 142, 143, 221, 151, 75; 24/30.5 T, 27

(56) References Cited

U.S. PATENT DOCUMENTS

| 3,535,746 A | * 10/1970 | Thomas, Jr. .............. 24/30.5 T |
| 3,675,688 A | 7/1972 | Bryan |
| 3,735,762 A | 5/1973 | Bryan |
| 4,485,816 A | * 12/1984 | Krumme .................. 606/221 |
| 5,026,379 A | 6/1991 | Yoon |
| 5,171,252 A | * 12/1992 | Friedland ................ 606/151 |
| 5,217,030 A | 6/1993 | Yoon |
| 5,217,472 A | 6/1993 | Green |
| 5,217,473 A | 6/1993 | Yoon |
| 5,226,908 A | 7/1993 | Yoon |
| 5,259,366 A | 11/1993 | Reydel |
| 5,330,483 A | 7/1994 | Heaven |
| 5,356,064 A | * 10/1994 | Green et al. ............. 606/139 |
| 5,733,329 A | 3/1998 | Wallace |
| 5,792,149 A | 8/1998 | Sherts |

FOREIGN PATENT DOCUMENTS

| EP | 121 362 | 10/1984 |
| WO | WO 92/13490 | 8/1992 |
| WO | WO 97/40755 | 11/1997 |

* cited by examiner

Primary Examiner—Julian W. Woo
(74) Attorney, Agent, or Firm—Bracewell & Patterson LLP

(57) ABSTRACT

A surgical apparatus and method for occluding or encircling a body passageway, e.g. for haemostasis, is described. The apparatus comprises generally a delivery system for offering a temperature-dependent shape memory material clip (3') (e.g. of Nitinol and suitably of generally U-shape in the open (a) condition) onto the body passageway, allowing body heat to warm the clip whereby the clip closes to a closed (b) condition in which it occludes or encircles the body passageway. The apparatus is then withdrawn from the operating zone. The apparatus includes drive and control functions for moving a train of clips (3') within a shaft (2') of the apparatus towards a distal end port (6'), and preferably a temperature control system whereby the clips within the housing are maintained at a first temperature, substantially below body temperature.

35 Claims, 16 Drawing Sheets (a)

(b)

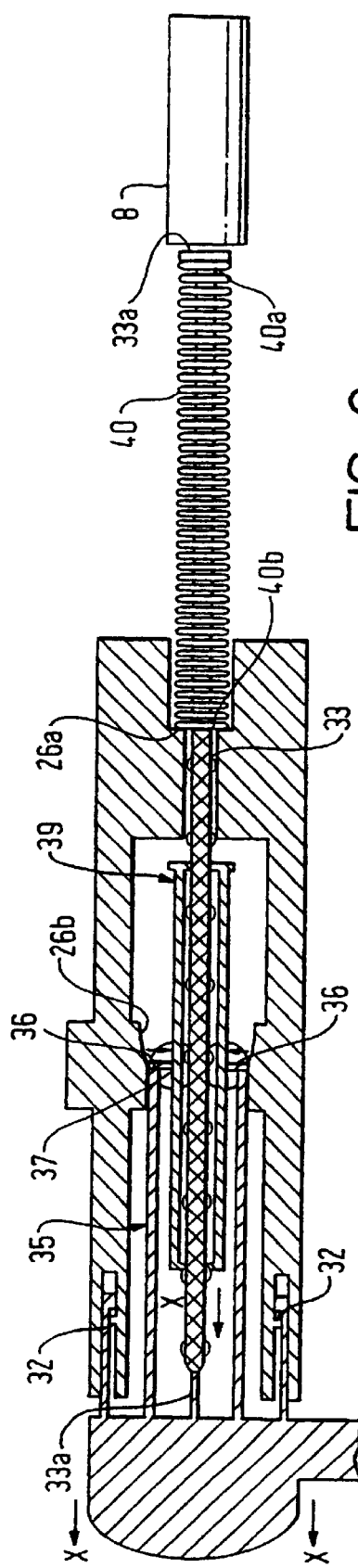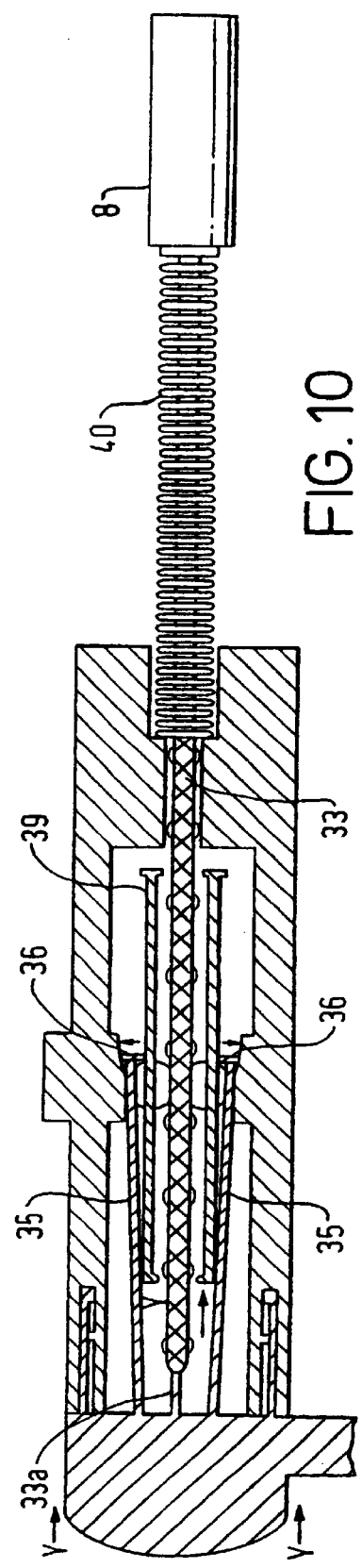

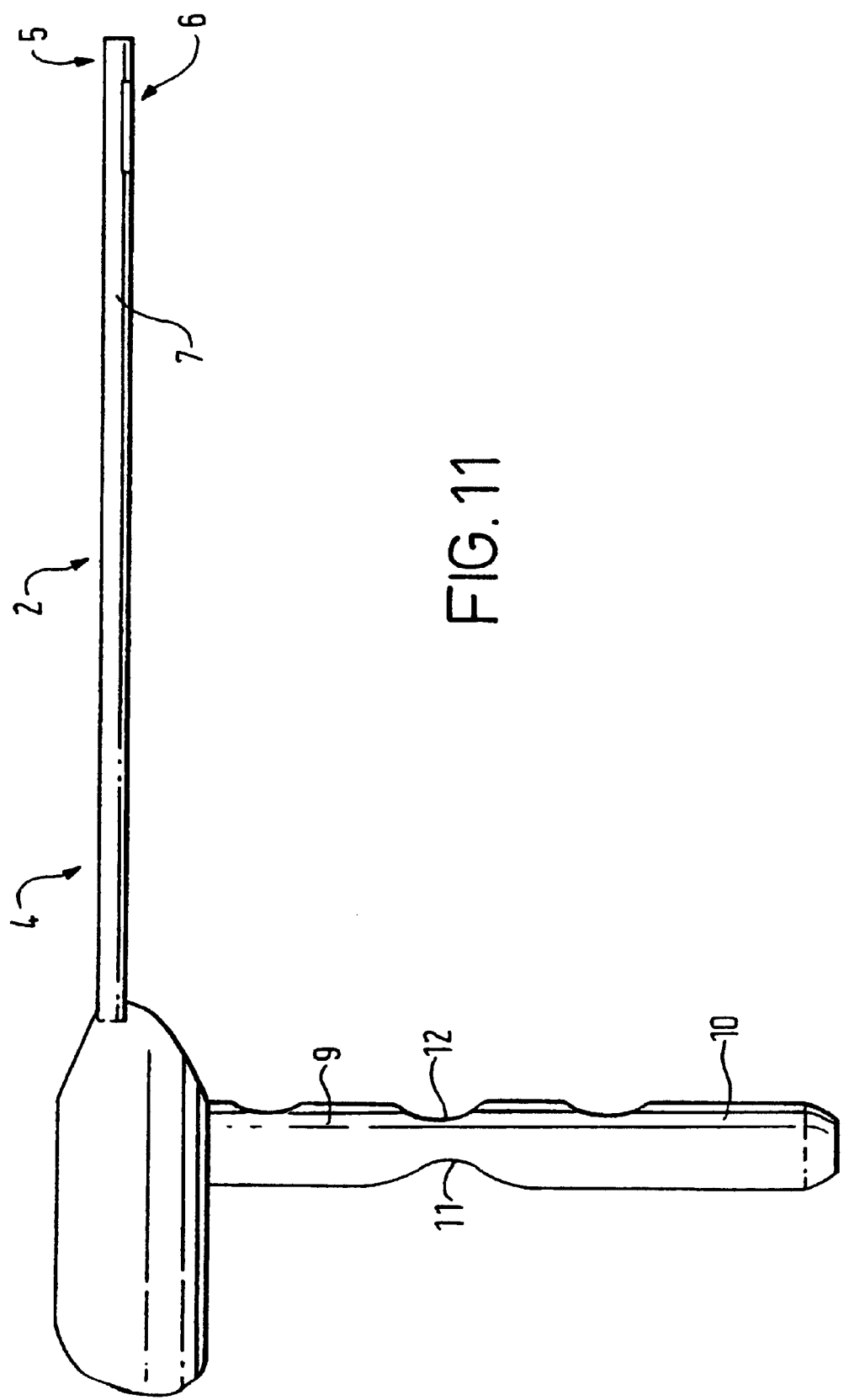

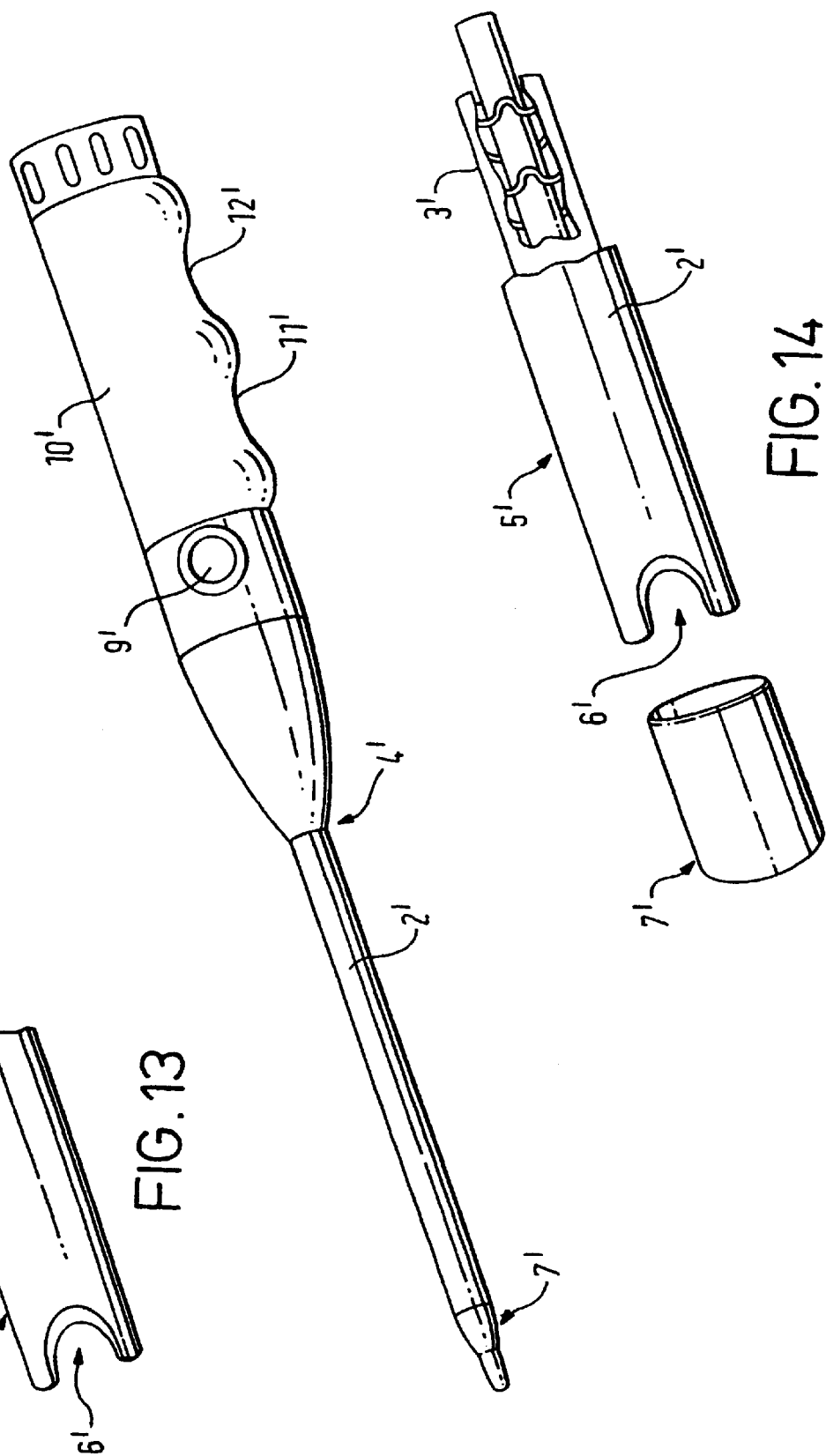

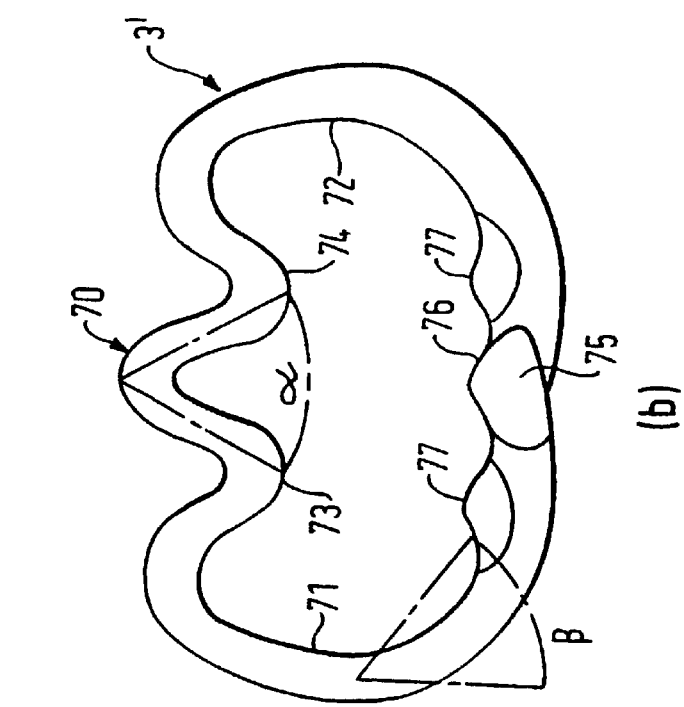
FIG. 19
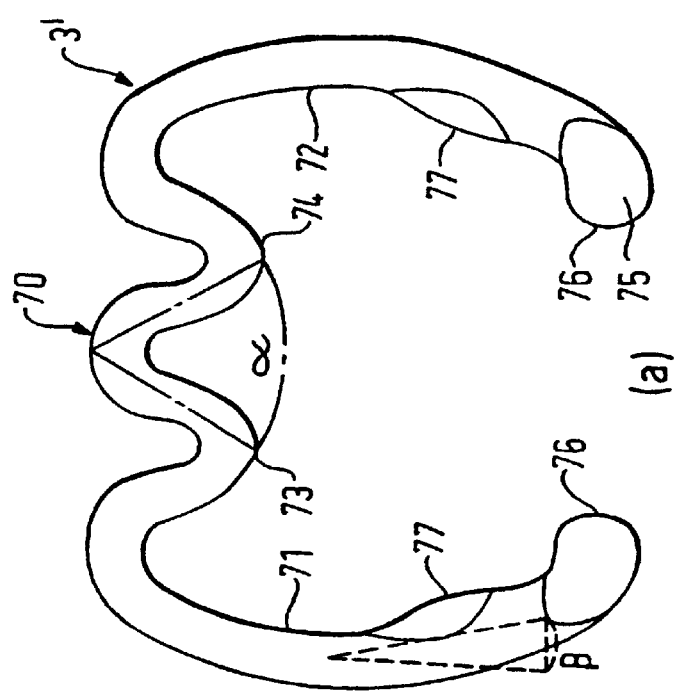
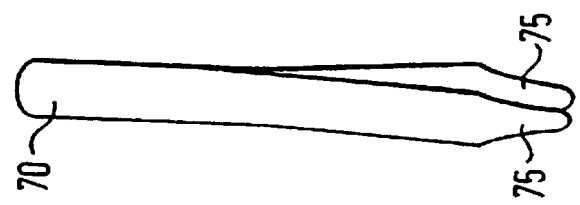
FIG. 21

SURGICAL APPARATUS AND METHOD FOR OCCLUDING OR ENCIRCLING A BODY PASSAGEWAY

FIELD OF THE INVENTION

The present invention relates to a surgical apparatus and method for occluding or encircling a body passageway such as a blood vessel. The invention further relates to surgical clips suitable for use in such an apparatus and method. The word "surgical" herein includes human and veterinary surgery and the word "patient" herein includes human and animal patients.

The word "occluding" herein includes complete or partial closure of a body passageway and the word "encircling" herein includes prevention of expansion of a body passageway without application of a constrictive force.

DESCRIPTION OF THE PRIOR ART

The surgical control of bleeding (haemostasis) by the closing of blood vessels is one of the oldest and most fundamental principles of surgery. Modern techniques such as minimally-invasive surgery cannot be performed without effective haemostasis, but there are significant difficulties in that the surgical instruments have to be controlled remotely from an operating zone within a patient and the surgeon is typically viewing the operating zone via an endoscope.

It is known to perform haemostasis during an endoscopic minimally-invasive surgical procedure by means of single sutures or ligatures tied around individual blood vessels. It is also known to use clips in the form of V-shaped lengths of silver wire which are cramped across the blood vessels. Sutures and ligatures are slow to apply as stitching or tying of individual threads is required, and the securement is technically difficult in endoscopic surgery. Silver clips are prone to dislodge.

Endoscopic staples are also Cloven for the occlusion of larger body passageways such as bronchi, the bile duct or bowel, but are too large for use on individual small vessels. Sprung clips have been used to occlude aortic aneurysms in conventional open (non-endoscopic) surgery, but are too large for use in endoscopic minimally-invasive surgery.

Thus, for example, U.S. Pat. Nos. 5,02,6379, 5,217,473 and 5,226,908 (Yoon), the disclosures of which are incorporated herein by reference, describe a ligating and occluding clip, useful in surgical sterilisation and other techniques, in which two straight legs are joined so that an elastic closing force closes the legs together across an anatomic tubular structure. These U.S. patents also describe an applicator device which releases the clip, legs splayed apart, onto the anatomic tubular structure. The elastic closing force causes the legs to close onto, and clamp, the anatomic tubular structure.

U.S Pat. Nos 3,675,688 and 3,735,762 (Bryan et al), the disclosures of which are incorporated herein by reference, describe a metal ligating and occluding staple which is wrapped around an anatomic tubular structure to occlude the same, as well as a cartridge applicator device from which staples are dispensed and which includes parts which cause each staple to be wrapped around the anatomic tubular structure and subsequently sever the structure.

U.S. Pat. No. 4,950,258 (Kawai et al), the disclosure of which is incorporated herein by reference, describes a range of surgical articles moulded from shape memory plastics, the articles including cerebral aneurysm clips (FIGS. 7 and 8a–8d) and a haemostatic clip (FIGS. 12a and 12b) which generally have two straight legs joined so that the shape memory effect causes a closing force to be exerted to close the legs together from a splayed apart condition (in which an anatomic tubular structure can be located within the clip) to a parallel condition (in which the anatomic tubular structure is constricted). The plastic material is biodegradable.

Apart from the biodegradability of the plastic material, which limits its utility to operations where only temporary occlusion or encircling of a body passageway is required, the surgical articles of U.S. Pat. No. 4,950,258 have a number of other disadvantages. The closing force is not particularly strong, so that the shape memory induced closure of the clips is slow and unreliable. Moreover, the straight-legged clips are unworkable in a confined operating zone. Still further, no practical applicator device is disclosed.

Other shape memory materials are known, which have been tested for use in the surgical occlusion or encircling of body passageways.

WO-A 92/13490 (Friedland), for example, describes a surgical fastening clip of a substantially U-shaped member of a shape memory metal alloy (eg Nitinol). The clip has an austenitic transformation temperature in the range of 30 to 35°, i.e just below normal body temperature. A range of clip designs is illustrated. FIG. 4, for example, shows a clip generally having two straight legs joined to form the general U-shape. In FIGS. 15 and 16, the legs are each kinked into a zig-zag shape. In FIGS. 20 and 21 the low temperature shape is straight-legged, the zig-zag shape appearing only in the austenitic state. A general feature of the clips is that in the austenitic shape the legs are tightly clamped together. The description teaches that the clips are to be squeezed down onto a vessel or tissue in the niartensitic (low temperature) state, whereupon heating to body temperature is allowed to occur to change the alloy to its austenitic state and "lock" the clip into the clamping condition (see, e.g. page 18, line 23 to page 19, line 7).

The disclosure of WO-A-92/13490 does not fully answer the needs of surgeons. The closing force of the clips is too small to be usable as an active occlusion and encircling system in a surgical procedure, i.e. where the clip itself closes onto a body passageway rather than being squeezed onto the body passageway by some external force. The need for an external force inherently limits the applicability of the prior art clips to surgical procedures where a clamping device can gain access to the operating zone. In any event, the disclosure does not clearly teach an applicator device whereby the clips can be located in place in a real surgical procedure and the transition from the martensitic to the austenitic states controlled in the body temperature environment of an operating zone within a patient's body.

U.S. Pat. No. 5,601,572 (Middleman et al), the disclosure of which is incorporated herein by reference, describes a surgical use of pseudoelastic shape memory alloys in which the memorised physical deformation takes place without additional squeezing or other pressure, and is an essential feature of the operation of a surgical instrument. "Pseudoelasticity" is a behaviour exhibited by shape memory alloys in a stress-induced martensitic condition. The instruments disclosed include a variety of devices in which generally an elongate member formed of a shape memory alloy is housed under stress within a hollow shaft of the instrument and extended from/retracted into a distal end of the shaft at an operating zone within a patient. In its extended condition the elongate member adopts its "memorised" shape, to perform a variety of surgical tasks.

In FIGS. 1–4 to 1–12 of U.S. Pat. No. 5,601,572, for example, and in the description accompanying those figures, a surgical instrument is illustrated and described, in which an elongate pseudoelastic shape memory alloy member is used to secure a ligature about a blood vessel, by extending the member from, and retracting it into, the hollow shaft of the instrument. The procedure is slow and complex, as well as being difficult to control in a confined operating zone.

WO-A 98/58591 (Boston Scientific Corporation; filed Jun. 17, 1998; published Dec. 30, 1998), the disclosure of which is incorporated herein by reference, describes a haemostatic clip formed of a material exhibiting pseudoelastic behaviour at body temperature. Such materials include shape memory alloys when in a stress-induced martensitic condition, and this reference describes the use of generally U-shaped staple-like haemostatic clips of such alloys which are individually held under stress with the legs of the clip forced into parallel alignment, at body temperature in an applicator device described as a "hypotube" (See FIGS. 1 to 5 and associated description). Upon release from the hypotube onto a blood vessel, the legs of the clip close together as the austenitic phase predominates and the memorised shape is adopted. A corresponding circular clip is illustrated in FIGS. 8 to 11, the clip being initially held confined in a curved hypodermic needle to stress-induce the martensitic condition. The closure of the clip is triggered by release of the stress, with no change in temperature.

The clips and applicators disclosed in WO-A-98/58591 suffer from a number of disadvantages. A prime difficulty is that a relatively complex applicator ejection system is required, because of the need to maintain the stored clip under stress before discharge.

This makes the applicator unwieldy, the release operation difficult for the surgeon, and limits the extent to which multiple clips can be loaded into the applicator for repeated use during a surgical procedure.

Therefore, no effective and secure method for occluding or encircling body passageways has been available hitherto which satisfies the requirements of (a) being usable on a wide range of body passageways from small blood vessels to large ducts, (b) being quick and easy to execute in all procedures, including open, micro and endoscopic procedures, and (c) being at least as reliable as the conventional methods.

The present invention aims to go at least some way towards meeting these requirements, or at least to provide an effective alternative to the known methods.

SUMMARY OF THE INVENTION

The invention is based on the finding that a clip, comprising an elongate element having first and second ends and being resiliently movable under an inherent biassing force between a first configuration in which the ends are spaced apart to allow a body passageway to pass therebetween and a second configuration in which the elongate element is deformed, preferably generally helically wound, on itself so that the clip grips or encircles the body passageway, can be released or offered towards the body passageway in the first configuration using a clip dispensing apparatus, whereupon the clip resiliently deforms itself around the body passageway to encircle and optionally constrict and occlude the same. The expressions "helical" and "generally helically wound", used herein, refer to at least one end of the clip bending inwardly around the body passageway, preferably to a condition where the ends are overlapping or crossing one another at least to some extent, and in particular are not to be considered as limited only to circular or cylindrical configurations Temperature-responsive shape memory materials, e.g. Nitinol alloys (nickel-titanium), are preferably to be used for this purpose. The preferred form of the present invention differs, however, from the prior art in that the transformation on which the shape memory is based is or includes the temperature-induced martensitic to austenitic transformation, as opposed to only the pseudoelastic or stress-induced martensitic to austenitic transformation. In particular, the clip is held in the dispensing apparatus at a temperature substantially below body temperature, and it is the body temperature of the operating zone that triggers closure of the clip. In addition, a novel clip shape is preferably employed, yielding substantial benefits in occlusion efficiency, and a novel applicator is also provided, in which preferably the thermal characteristics, for example conductivity, of the operating mechanism of the applicator itself contributes positively to the functioning of the clip.

The various features of the invention are as set forth in the claims appended hereto, allowing for any principles of interpretation of those claims as prescribed by law.

DETAILED DESCRIPTION OF THE INVENTION

Thus, in a first aspect of the present invention, there is provided a surgical apparatus for occluding or encircling a body passageway, the apparatus generally comprising:

(a) a housing holding one or a plurality of clips of the type described above in the first configuration thereof, the housing having a port through which an individual clip can be released to occlude or encircle the body passageway;

(b) a drive member disposed within the housing and movable therein to urge a clip within the housing towards the port thereof, and (c) a clip control device associated with the drive member and operable externally of the housing to control the movement of the clip therein and expulsion of the clip therefrom.

The clip control device is so arranged and/or the port of the apparatus is so configured that only one clip can pass through the port in any one operation of the clip control device.

Particularly when the apparatus is to be used in endoscopic surgery, the housing suitably comprises a hollow shaft having a proximal end and a distal end, the port being provided at or near the distal end and a handle being provided at or near the proximal end, in general proximity to the control device, whereby a surgeon can hold the apparatus.

It is preferred, although not essential, that the clips are held in a line within the hollow shaft of the housing and driven in that line towards the open distal end. Alternatively, for example, they can be held in a magazine and fed into the shaft one by one by clip feeding means. The clips are conveniently provided as a train of generally like clips, all similarly oriented in the train. In some cases, the clips can conveniently be mutually frangibly connected to form a cartridge which can be loaded into the shaft or magazine. A guide member may suitably be provided in the housing, which guide member supports the clip(s), slidably within the housing, in a location whereby the drive member can urge the clip(s) towards the port of the housing.

When referring to the elongate element of the clips for use in the device of the present invention, the expression "resilient" and like expressions used herein shall be taken to refer to all forms of inherent or internal (molecular) biassing of the elongate element of the clip towards its second configuration. For example, a biocompatible temperature-responsive "shape-memory" material can be used, in which the resilience is activated by a change (typically a rise) in temperature, so avoiding the need for the clip to be held in its first configuration against a restoring force. The "memorised" shape will be the second, e.g. helical, configuration. The "shape-memory" material may, for example, be a metallic alloy such as Ti—Ni, Ni—Al, Ag—Cd or Au—Cd, a norbornene polymer, a nematic liquid crystal polymer, or an advanced thermoplastic elastomer such as a homopolymer of lactide or glycolide or copolymers thereof. For further discussion of these materials, please refer to U.S. Pat. Nos. 3,442,871, 3,797,499, 3,839,297,4,505,767,4,523,591, 4,603,695 4,935,068 and 4,950,258, as well as British Patent No. 1040168 (the disclosures of all of which are incorporated herein by reference), in addition to the prior art acknowledged above.

In summary, and as will be well known to those of ordinary skill in this art, shape memory alloys are capable of transforming between martensitic and austenitic phases. This transformation between phases can be caused by a change in temperature. For example, a shape memory alloy in the martensitic phase will begin to transform to the austenitic phase when its temperature rises above the austenite start temperature $A_s$, and the transformation will be complete when the temperature rises above the austenite finish temperature $A_f$. The transformation from austenitic to martensitic will begin when the temperature drops below the martensite start temperature $M_s$, and will be complete when the temperature drops below the martensite finish temperature $M_f$. The temperatures $M_s$, $M_f$, $A_s$ and $A_f$ define the thermal transformation hysteresis loop of the shape memory alloy, and can be adjusted with a relatively high degree of precision, in the case of Ti—Ni alloys by adjustment of the relative proportions of the nickel and titanium.

The preferred material is a biocompatible and magnetic resonance imaging (MRI-) compatible temperature-dependent shape memory material having a shape transition temperature (martensite-to-austenite) in the range of approximately 20–35° C. This means that $A_f$ should be no greater than about 35° and $A_s$, should preferably be no less than about 20° C., e.g. less than about 15° C. Such a material is Nitinol, which is a nickel-titanium alloy comprising approximately 50 atomic percent nickel. For example, the alloy may be a binary alloy consisting of 50.8 atomic percent nickel and 49.2 atomic percent titanium, or it may include a quantity of a third element such as copper, cobalt, vanadium, chromium or iron. The binary alloy is preferred, as the more complex systems generally have inferior biocompatability.

Alternatively, however, a temperature-dependent shape memory plastic of the types disclosed in the acknowledged prior art can be used.

Such clips should be stored in the martensite phase at a reduced temperature (preferably below about 20° C., e.g. below about 15° C.), so that, on deployment into the operating zone within the patient, the patient's body temperature rapidly heats the clip to a temperature above the martensite-to-austenite shape transition temperature, preferably above $A_f$. This has been found to impart a closing force of up to 200 grams force onto the body passageway as the ends of the clip close to the second configuration of the clip. In this way, the closing force can be tailored to the intended end use of the clip, e.g. a crushing force (for haemostasis, for example) or a non-crushing force (for occluding body ducts, e.g. in sterilisation).

At least the central portion of the clip, between the ends thereof, is preferably formed of the resilient material. Preferably the whole clip is formed of the resilient material.

The said central portion of the elongate element of the clips is typically in the range of about 1 to 30 mm in length, depending on the intended use of the invention. The arrangement should preferably be such that in use the elongate element twists, e.g. helically, around a body passageway to match the size of the body passageway (encircling) or with a sufficient constrictive force thereon to occlude (at least partially close) the body passageway. The selection of the precise material and dimensions of the elongate element for this purpose will be well within the capabilities of one of ordinary skill in this art.

The first and second ends of the clip preferably comprise legs extending in the same general direction as each other from the intermediate central portion, the intermediate central portion being most preferably convoluted as will be described in more detail below. The term "generally the same direction" used herein refers to directions which are broadly similar, i.e. less than about 120° separated, preferably less than about 45° separated. This configuration will be referred to herein as a generally U-configuration.

The clips are very convenient for surgical placement, achieving potentially up to about twice or three times the opening distance of conventional surgical clips. It is most preferred that the ends of the legs of the clip in the first configuration thereof should be spaced apart by no more than about 4 times the external diameter of the body passageway, more preferably no more than about 3 times the said diameter, and most preferably between about 1.5 and about 2.5 times the said diameter.

The legs of the clip in the first configuration thereof may be straight or curved, or may have straight and curved regions along their length.

The ends of the elongate element of the clip may conveniently be somewhat enlarged so that the clip in a fully straight configuration (which is not necessarily achievable in practice but may be only theoretical) would have the general appearance of a miniature weightlifter's dumbbell. The surfaces of the ends of the elongate element of the clip may be formed of a tough, low-friction, high-abrasion-resistance material such as, for example, ultrahigh molecular weight polyethylene. The ends of the clip can slide over each other, optionally with a cam action, as the clip deforms into its second (helical) configuration. The folded-over ends of the clip are thus securely fastened in the second configuration to encircle or constrict the body passageway.

The elongate element of the clip between its ends may, for example, be of generally cylindrical, rectangular, triangular or square cross-section.

In a particularly preferred form, the tightness of the helical winding is such that the diameter of curvature is less than about 2 mm. It is preferred that the elongate element should not close on itself completely, as this would carry a risk of severing the body passageway. The extent of closure will be readily selectable according to the dimensions and materials of the clip, and this is well within the abilities of one or ordinary skill in this art.

The clips may be permanent in the sense of non-absorbable by the patient's body, or biodegradable (absorbable) within the patient's body.

In their first configuration, the clips may, for example, be aligned longitudinally (end-to-end) or transversely (side-by-side). Where the first configuration of the clips is a generally U-configuration, the clips may be in chevron alignment nested together.

The preferred clip shape will now be described in more detail.

In the first (low temperature) configuration, the clip may suitably be in the general form of a staple, and preferably has a convoluted, e.g. a zig-zag or sinuously curved, central portion, formed preferably of Nitinol wire, e.g. of substantially circular cross section. For a clip having legs approximately 2 mm apart in the first configuration the Nitinol wire may suitably have a cross-sectional diameter of approximately 0.3 mm, and correspondingly larger or smaller clips will use correspondingly thicker or thinner wire. The convoluted central portion has at least one, preferably two, three or more, apices directed towards the legs of the clip. These apices provide shoulders against which the legs in the second (body temperature) configuration can urge the body passageway.

The convoluted central portion has the further desirable property that it permits the central portion of the clip to expand sideways slightly in the second configuration (e.g. by a flattening of the sinuous curves) so allowing the legs to clasp towards the central portion of the clip with a good angular presentation and therefore good mechanical advantage.

The legs of the clip are preferably integral with the central portion and consist of the same Nitinol wire, extending in generally the same direction as each other in the first configuration of the clip and lying preferably in substantially the same plane as the convolutions of the central portion. In the first configuration of the clip, the legs preferably turn slightly mutually inwards and at their ends they are preferably each provided with a wedge surface with suitably terminates to a wedge apex line at the end of the respective leg. This wedge apex line may suitably be approximately parallel with the corresponding wedge apex line of the opposing leg of the clip.

A little way along each leg from the terminal wedge surface there may suitably be provided an enlarged inwardly directed nip-head projection, which may for example be rounded. This nip-head projection is arranged to bear towards one of the inwardly directed apices of the convoluted central portion of the clip in the second configuration of the clip, to maximise the pinching effect of the closure of the legs towards the central portion as the clip moves into the said second configuration.

In moving towards the second configuration of the clip, the convolutions (e.g. the zig-zag or sinuous curve) of the central portion of the clip may straighten somewhat, accompanied by a slight reduction in the amplitude of the zig-zag or sinuous curves (e.g. by about 0.1 to about 2 percent) and the legs close towards each other so that the wedge surfaces slide over one another. For this purpose, the wedge apex lines may suitably be slightly offset from one another out of the plane of the clip in the first configuration, so that they will not meet each other precisely square-on during the closing movement. In addition, the closing movement involves the ends of the legs moving towards the central portion, so that the nip-head projection of each leg urges the body passageway towards an inwardly directed apex of the convoluted central portion. This movement of the ends of the legs inwards towards the central portion may suitably have the effect of reducing the external dimensions of the clip (back of the central portion to front of the legs) by approximately 10 to 80%. Where the body portion has a zig-zag or sinuous curve, the percentage reduction in the dimension of the clip may be towards the lower end of the range, e.g. about 10 to 30%, as the amplitude of the zig-zag or sinuous curve may itself constitute up to about 40 to 50% of the dimension, and this amplitude typically changes only marginally as the convolutions of the central portion straighten slightly, as described above.

As will be well known to those skilled in the art, the clips of the present invention will suitably be first formed in their second (austenite) configuration, e.g. by cutting and press-forming the Nitinol wire and bending the resulting form to shape, and the temperature is then lowered to below the austenite-to-martensite transition temperature (i.e. to below $M_f$). The alloy atomic structure changes to the weaker martensite form, and the material can easily be deformed to a new shape, namely the first configuration.

Martensitic transformation comes about not through nucleation and growth (as in most crystal structure transformation of metals and alloys). Instead, it occurs through a much faster collective shear process, The transformation of interest in the present invention is the temperature-induced martensitic transformation. The alternative possible stress-induced or mechanical martensite transformation, and the pseudoelasticity and superelasticity that it produces, is not necessarily a requirement of the present invention.

It is an important preferred feature of the apparatus that the distal clip, prior to expulsion from the apparatus, is held in the port of the housing in its first (open) configuration, adjacent to the body passageway to be occluded or encircled and in such a way that the ends of the clip are free to deform onto the body passageway without external pressure to close the clip. Once the closing movement has sufficiently advanced, the apparatus can be withdrawn, without any internally driven propulsion of the clip from the housing. The expression "expulsion" or "expelled" used herein to describe the dispensing of the distal clip from the apparatus, includes all forms of release, including passive dispensing in this sense, i.e. the withdrawal of the apparatus from the operating zone so as to leave the clip in place on the body passageway.

The housing of the apparatus holds and supports one or more, preferably a plurality, of the clips in the first configuration thereof. The plurality of clips may be in a line with the clips aligned longitudinally (end-to-end) or transversely (side-by-side). Alternatively, a plurality of generally U-configuration clips may be in a chevron-like line. An even number of clips may suitably be used, particularly for procedures where body passageways need to be occluded at two points along their length. This prevents accidental exhaustion of the supply of clips during the procedure.

Certain clips in the first and/or second configurations thereof are novel, irrespective of whether the material from which the clip is constructed is a temperature-responsive shape memory material or any other resilient material such as, for example, a conventional elastomer. These clips constitute further features of the present invention, and while their presentation to a body passageway may be accompanied by a rise in temperature as the clip warms to the temperature of the operating zone, this temperature rise is not an essential pre-requisite for the closing of such clips into the second configuration thereof.

Thus, according to a further aspect of the invention, there is provided a surgical clip for occluding or encircling a body passageway, the clip comprising an elongate element having first and second ends and an intermediate central portion, the clip comprising a resilient material and being resiliently movable under an inherent biassing force from a first configuration, in which the ends are spaced apart to allow the body passageway to pass therebetween, to a second configuration in which the clip is deformed, preferably generally helically wound, on itself so that the clip grips or encircles the body passageway, wherein:

(a) the first and second ends of the clip are legs which in the second configuration of the clip are turned inwardly toward the intermediate central portion of the clip, whereby the body passageway is gripped between the legs and the intermediate central portion of the clip, or encircled by the legs and the central portion of the clip, the intermediate central portion being convoluted in at least the said second configuration;

(b) the first and second ends of the clip are adapted, for example enlarged, so that in moving from the first to the second configuration the ends of the clip can slide over each other, optionally with a cam action, as the clip deforms into its second configuration;

(c) the first and second ends of the clip are legs which are provided with enlarged nip-head projections along their lengths, whereby in the second configuration of the clip the projections nip the body passageway against the intermediate central portion of the clip;

(d) the first configuration of the clip is substantially rectilinear and the second configuration of the clip is preferably generally helically wound on itself, whereby if the clip comprises an elastomeric material, the first configuration is achievable by holding the clip constrained in the said rectilinear configuration against a resilient restoring force tending to move the clip into the second configuration thereof; or (e) any combination of (a) to (d) above.

The housing preferably comprises a thermally insulating hollow shaft containing the clips and the drive member, the port being an open distal end of the shaft. In this preferred form of the invention, the cover member for the port is preferably a thermally insulating cup or thimble arrangement which can be manually removed for use, and replaced when the apparatus is not in use. This cover member is desirable so that temperature-responsive clips in the housing do not warm up prematurely.

Alternatively, the cover member may be moved into and out of position by use of a cover member control device operable externally of the housing. In a preferred form of such an arrangement, the clip control device and the cover member control device are synchronised and actuable by a single action of the surgeon. In such an arrangement, the cover member for the port of the housing preferably takes the form of a retractable shutter, movable back and forth in response to actuation of the cover member control device. The shutter preferably has a closed portion which serves to cover the port of the housing when the closed portion and port are correspondingly aligned and an open portion which serves to uncover the port when the open portion and port are correspondingly aligned. By providing a retractable cover member at the port of the housing, and by synchronising the clip control device and cover member control device so that the drive member of the apparatus can only operate on the clips when the port is covered, there is no possibility of causing more than one clip to become available to be released through the port in on "firing" (i.e. actuation) by the surgeon.

In a preferred form of the invention, therefore, the apparatus further comprises:

(d) a cover member for the port of the housing, the cover member being movable selectively to cover or uncover said port; and optionally (e) a cover member control device operable externally of the housing to control the movement of the cover member and thereby the expulsion of the clip from the housing.

The apparatus preferably includes a temperature control device for maintaining the clip(s) at the first temperature within the housing. The temperature control device may include a thermostat, for automatic fine control of temperature within the housing. Suitable temperature control devices include electronic semiconductor-based cooling devices which use the Peltier effect, or gas-expansion-based cooling devices which use the Joule-Thompson effect. The parts of the clip drive and control means which support and contact the clips may suitably be thermoconductive (e.g. metallic), and in thermal contact with the temperature control device, whereby the temperature of the clips themselves can be effectively controlled.

The drive member for urging a clip within the housing towards the port thereof suitably comprises a push member (e.g. a pressor rod) disposed at least partially upstream of the clips to be slidable within the housing to urge against the line of clips within the housing. The push member is preferably spring biassed. The distal clip preferably lies in an expulsion station adjacent the port, from which it can be released from the apparatus either by its own inherent tendency to twist out of its holding alignment or by an expulsion element provided in the apparatus. For example, an expulsion element may be required to break any frangible connections in a cartridge of clips. The line of clips is preferably oriented about its axis in such a way that the ends of the distal clip will tend to move (twist) away from the port of the apparatus and around any adjacent body passageway.

The clip control device of the apparatus are preferably manually operable by the surgeon (e.g. by finger pressure on a button or trigger). The control of clip movement and expulsion is of great importance to the success of the apparatus, as the consequences of incorrect "firing" of the apparatus would be catastrophic for a patient.

The clip control device of the apparatus preferably comprises a ratchet or cam device associated with the push member and operably linked to the remainder of the clip control device. In one preferred form, a spring forwardly biasses the push member, the spring being releasable from contact with the push member, and the ratchet or cam device serves in each actuation of the clip control device to take the spring out of contact with the push member when the port is open, thereby removing any spring-loaded forward pressure on the clips while the port is open. In another preferred form, a spring rearwardly biasses the push member, and the ratchet or cam device serves in each actuation of the clip control device to urge the push member in the forward direction (against the restoring force of the spring), which again serves to locate the distal clip in the port of the housing without any forward pressure on the clips while the port is open.

When the housing comprises a shaft, e.g. in the case of a device for use in endoscopic surgery, the port of the shaft may, for example, be present at its distal end face or a side port may be provided in the wall of the shaft near its distal end. In the first form, the shaft can be pushed onto a body passageway before a clip is expelled onto the body passageway. However, in this configuration the surgeon's endoscopic view of the body passageway may be obscured by the shaft of the apparatus of the present invention. In the second form, which may avoid this disadvantage, the apparatus may be brought alongside the body passageway before the apparatus is actuated.

The apparatus may be constructed from any convenient materials. Metals such as, for example, stainless steel may be used. Plastic polymers such as, for example, ultrahigh molecular weight polyethylene or polyacetyl may be used. Of course, different materials may be used for different parts. Metal is preferred for the internal mechanism, with plastic preferred for the outer housing.

As mentioned above, the apparatus may conveniently be provided with a proximal handle whereby the surgeon can hold the apparatus. The clip control device and, if present, cover control device are preferably actuable via a single finger trigger or button associated with the handle. The ergonomically configured handles and finger-control systems described in WO-97/42884 are particularly suitable, and the disclosure of that earlier publication is incorporated herein by reference.

Moreover, when used in endoscopic surgery, the device may conveniently be used with the improved instrument support systems for endoscopic surgery described in WO-97/42884.

The apparatus may suitably be provided in disposable and reusable parts, which are releasably connectable together for use. The "disposable" part(s) is/are suitably provided in sterile individual packs, and the "reusable" part(s) is/are suitably provided in sterilisable materials and in an sterilisable configuration.

The disposable part(s) may suitably include the clips, and may for example comprise at least a major portion of the shaft of the housing in the preferred apparatus form. The clips may be pre-loaded in the shaft, so that all that is necessary for the surgeon or his or her assistant to do is to connect the disposable shaft to the reusable handle part. Alternatively, the disposable part may comprise a magazine or cartridge of clips, which is loaded into reusable apparatus.

Where it is convenient, and where suitable laboratory or workshop facilities are available the "disposable" part(s) may in fact be made recyclable, e.g. reloadable With clips, resettable into the ready-for-use configuration, and resterilisable.

One particular surgical method for occluding or encircling a body passageway, enabled by the apparatus of the present invention, generally comprises:

(a) providing a clip comprising an elongate element having first and second ends and an intermediate central portion, the clip comprising a temperature dependent shape memory material and being resiliently movable, in response to an increase in temperature from a first temperature, substantially below body temperature, to body temperature, under an inherent biasing force from a first configuration, in which the ends are spaced apart to allow the body passageway to pass therebetween, to a second configuration in which the clip is deformed on itself so that the clip grips or encircles the body passageway, the clip being provided at the first temperature and in the first configuration thereof;

(b) offering the clip to the body passageway so that the body passageway is received substantially between the ends of the clip; and (c) allowing the temperature of the clip to rise to approach body temperature by the proximity of the body passageway to the clip, whereby the clip deforms into its second configuration around the body passageway.

In another aspect, the surgical method for occluding or encircling a body passageway, using the apparatus of the present invention, generally comprises:

(a) locating the surgical apparatus such that the port of the housing is in proximity to the body passageway;

(b) operating the clip control device to cause a clip to be expelled from the port of the housing of the apparatus, whereby upon release in its first configuration from the apparatus the clip resiliently deforms itself onto the body passageway to occlude or encircle the body passageway; and (c) removing the apparatus from proximity to the body passageway.

BRIEF DESCRIPTION OF THE DRAWINGS

For ease of understanding the present invention, embodiments will now be described, without limitation and purely by way of example, with reference to the accompanying drawings, in which:

FIGS. 9 and 10 show the part of FIG. 6 at different stages of the trigger actuation and release cycle;

FIG. 11 shows the outward design appearance of the apparatus of FIG. 1 with the trigger in the resting condition and the port closed;

FIG. 12 shows a perspective external view of an alternative surgical apparatus for occluding or encircling a body passageway, with a first design of distal end cover;

FIG. 13 shows in perspective view the apparatus of FIG. 12 with the distal end cover removed;

FIG. 14 shows a detail of the distal end of the apparatus of FIG. 12, with a partial cut away view of clips within the shaft, the distal end cover being to a second design;

FIG. 15b shows a vertical cross-sectional view of the distal end cover of FIG. 15a;

FIG. 19 shows the clip present in the apparatus of FIGS. 12 to 18, (a) in its first (low temperature) configuration and (b) in its second (body temperature) configuration;

FIG. 21 shows a side view of the clip of FIG. 19(a), looking from the left.

DETAILED DESCRIPTION OF THE DRAWINGS

Figure 1:
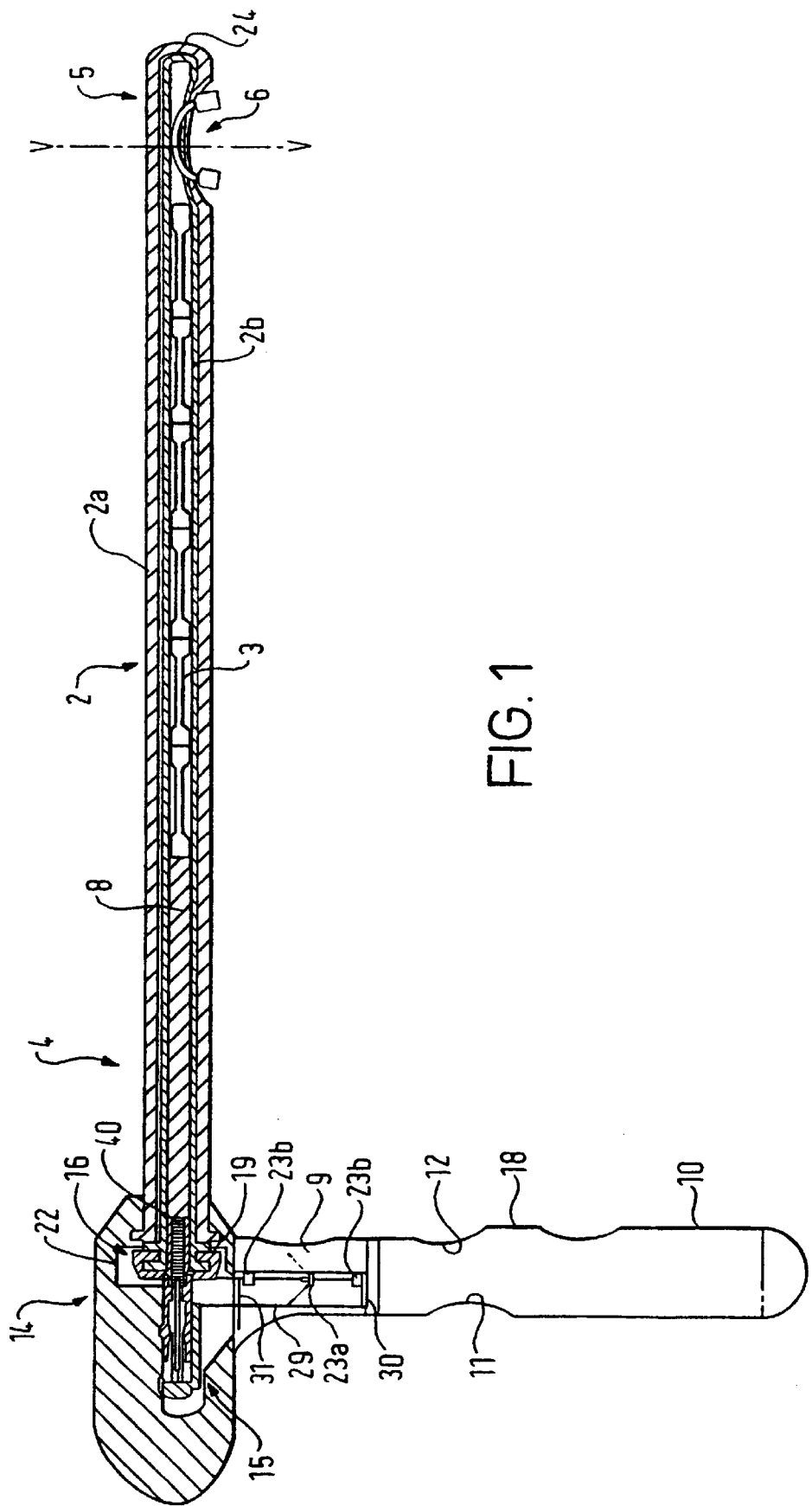
FIG. 1 shows in partial vertical cross-section a surgical apparatus for occluding or encircling a body passageway.
Figure 2:
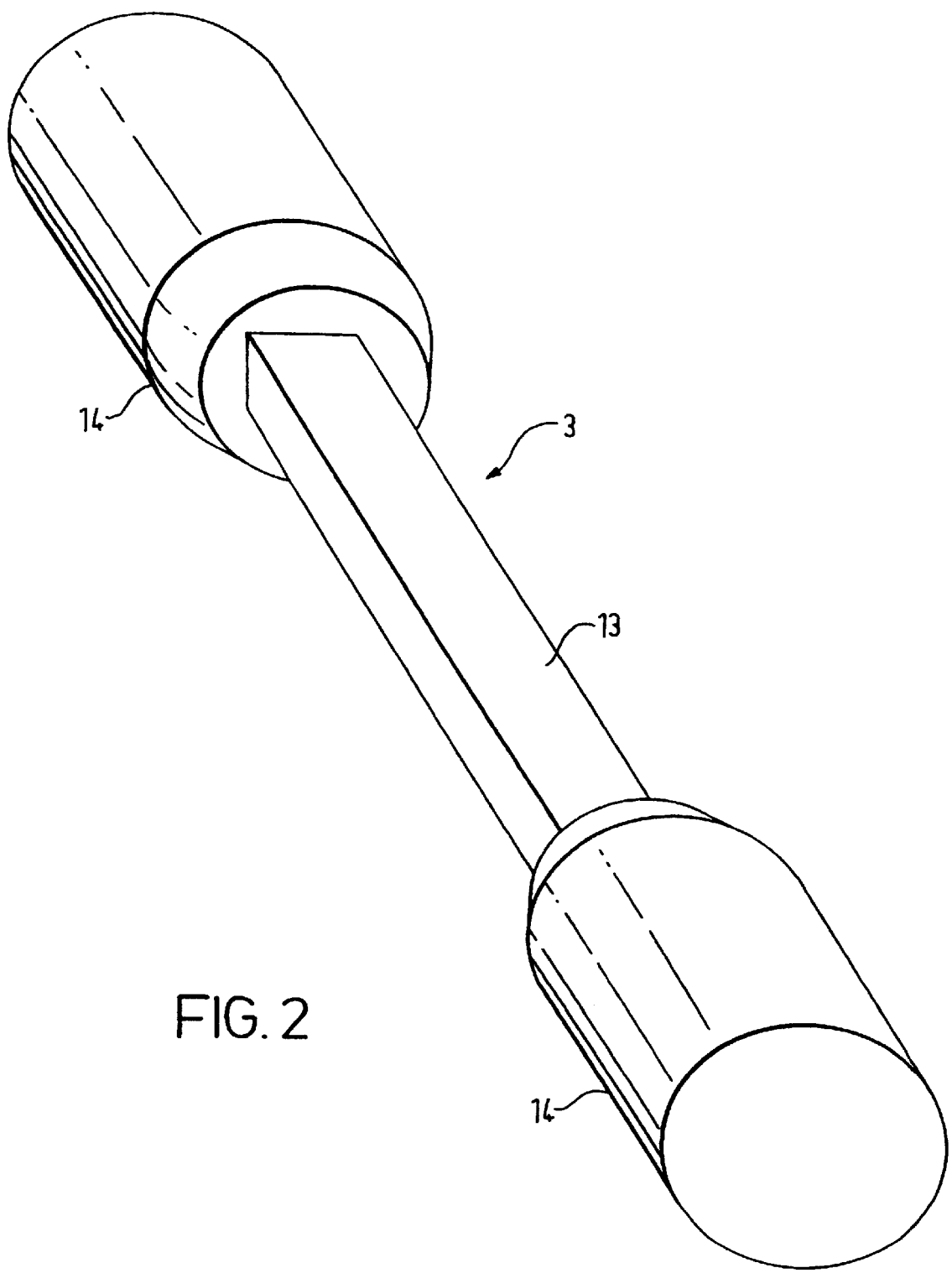
FIG. 2 shows in artificially-transparent detail a clip used in the apparatus of FIG. 1, in its first (straight) configuration.

Referring firstly to FIGS. 1 to 11 of the drawings, a surgical apparatus for occluding or encircling a body passageway 1 (e.g. a vein or artery) during endoscopic surgery comprises a housing in the general form of a hollow shaft 2 holding a line of surgical clips 3. The apparatus will be described herein only with reference to at least partial occlusion of the body passageway. Encirclement of a body passageway without constriction can be achieved by selecting the appropriate tightness of winding of the helical configuration of the clip. The shaft 2 has a proximal end 4 and a distal end 5. The distal end 5 of the shaft 2 is provided with a port 6 through which an individual clip 3 can be released. The port 6 is openable and closable by means of a cover member 7 for the port, the cover member 7 being movable selectively to cover or uncover the port by means of cover member control means operable externally of the housing to control the movement of the cover member. The cover member control means will be described in more detail below.

In the apparatus of FIGS. 1 to 11 there is no internal temperature control device. This apparatus is suitable for use in a relatively cool ambient environment, or in conjunction with a cool holster in which the apparatus is held when not in use.

Drive means comprising a releasably spring-biassed pressor rod 8 are disposed within the shaft 2 and are slidable along the inner space of the shaft to urge the line of clips 3 within the shaft towards the port 6. The spring biassing, when applied in the resting condition, urges the pressor rod 8 towards the line of clips (to the night as viewed in FIG. 1), as will be described in more detail below. The pressor rod 8 thus senses to position the distal clip of the line at an ejection station at the distal end of the shaft 2, from which, using the inherent tendency of the clip to twist, it can be released through the open port 6 of the shaft. The line of clips is orientated about its axis in such a way that the ends of the distal clip will tend to twist out of the apparatus and around any adjacent body passageway 1. It should be noted that the clip is not actively pushed out of the apparatus; it curls around the body passageway in response to the temperature rise in the operating zone adjacent the body passageway, and the apparatus can then be withdrawn to leave the clip in place.

The apparatus includes clip control means which comprise means for controlling the said movement of the pressor rod within the shaft. These clip control means are synchronised with the cover member control means. More particularly, and as will be described in greater detail below, the spring biassing is released from the pressor rod 8 whenever the port 6 is open, thereby removing any urging force on the line of clips 3, to prevent multiple expulsion of clips. In this way, the movement of the clips in the shaft 2 and their individual expulsion from the port 6 of the shaft 2 can be controlled from the proximal end of the device by the surgeon. The control means are operable externally of the apparatus via a finger-actuable trigger button 9 mounted on an ergonomically configured handle 10 for the apparatus. The handle 10 is provided with surface depressions 11, 12 whereby a surgeon can grip the handle fast between thumb and middle finger, and is sufficiently short that the surgeon can freely move the palm of his or her hand over and around the end of the handle without releasing the grip on the handle.

The line of clips 3 will now be described in detail. In the embodiment shown, each clip of the line is discrete from its neighbour, although a frangibly-connected line of clips can alternatively be envisaged. Each clip 3 comprises a central elongate element 13 having somewhat enlarged first and second ends 14, giving it the general appearance of a miniature weightlifter's dumbell.

The clip may be formed of a "shape-memory" biocompatible polymer, preferably by moulding, and if necessary the ends 14 may be provided with a coating of ultrahigh molecular weight polyethylene, although "memory" metal may, for example, alternatively be used. This provides a low-friction surface when the enlarged ends slide over one another in a cam action as the clip closes around the body passageway 1.

Figure 3:
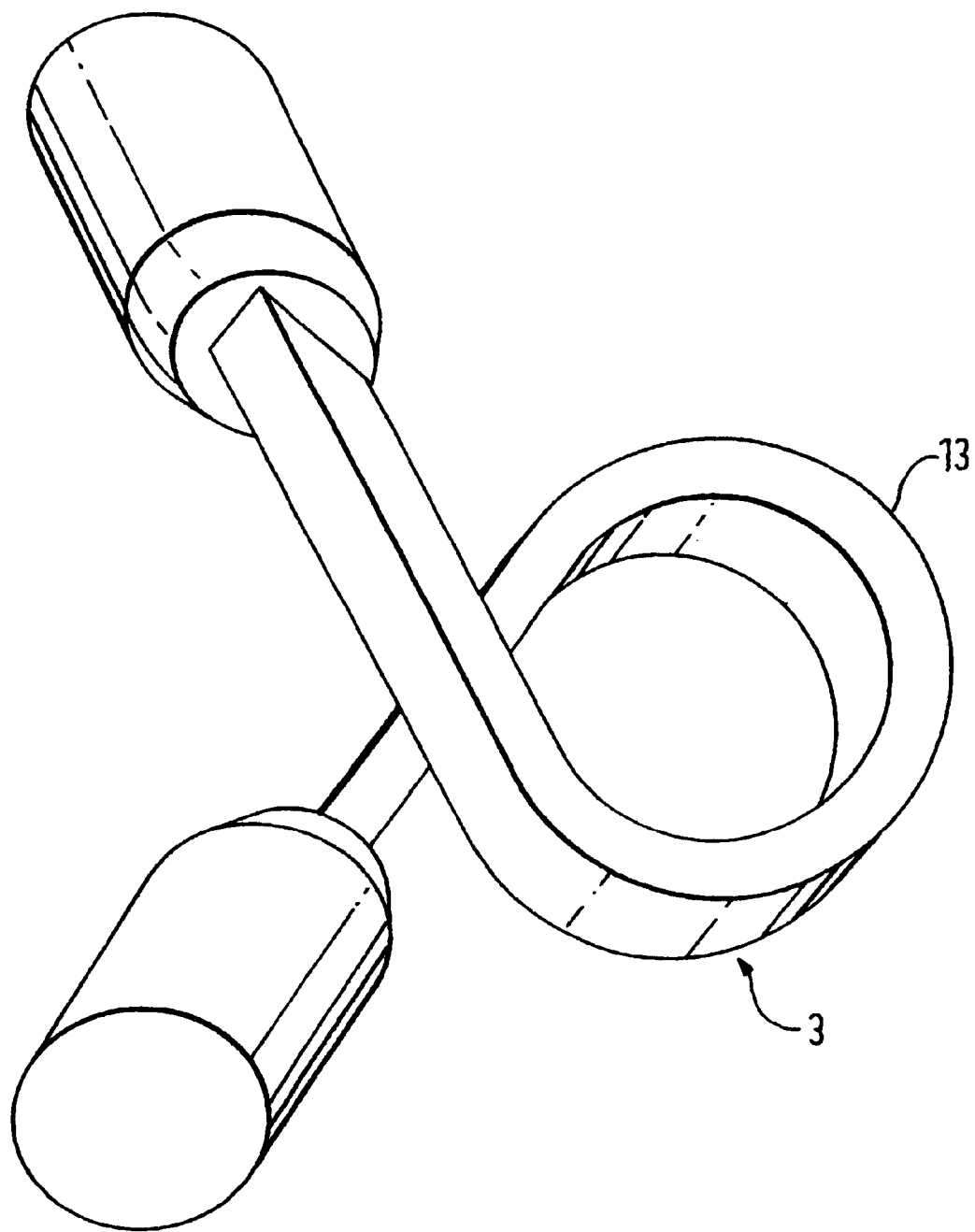
FIG. 3 shows the clip of FIG. 2 in its second (helical) configuration.
Figure 4:
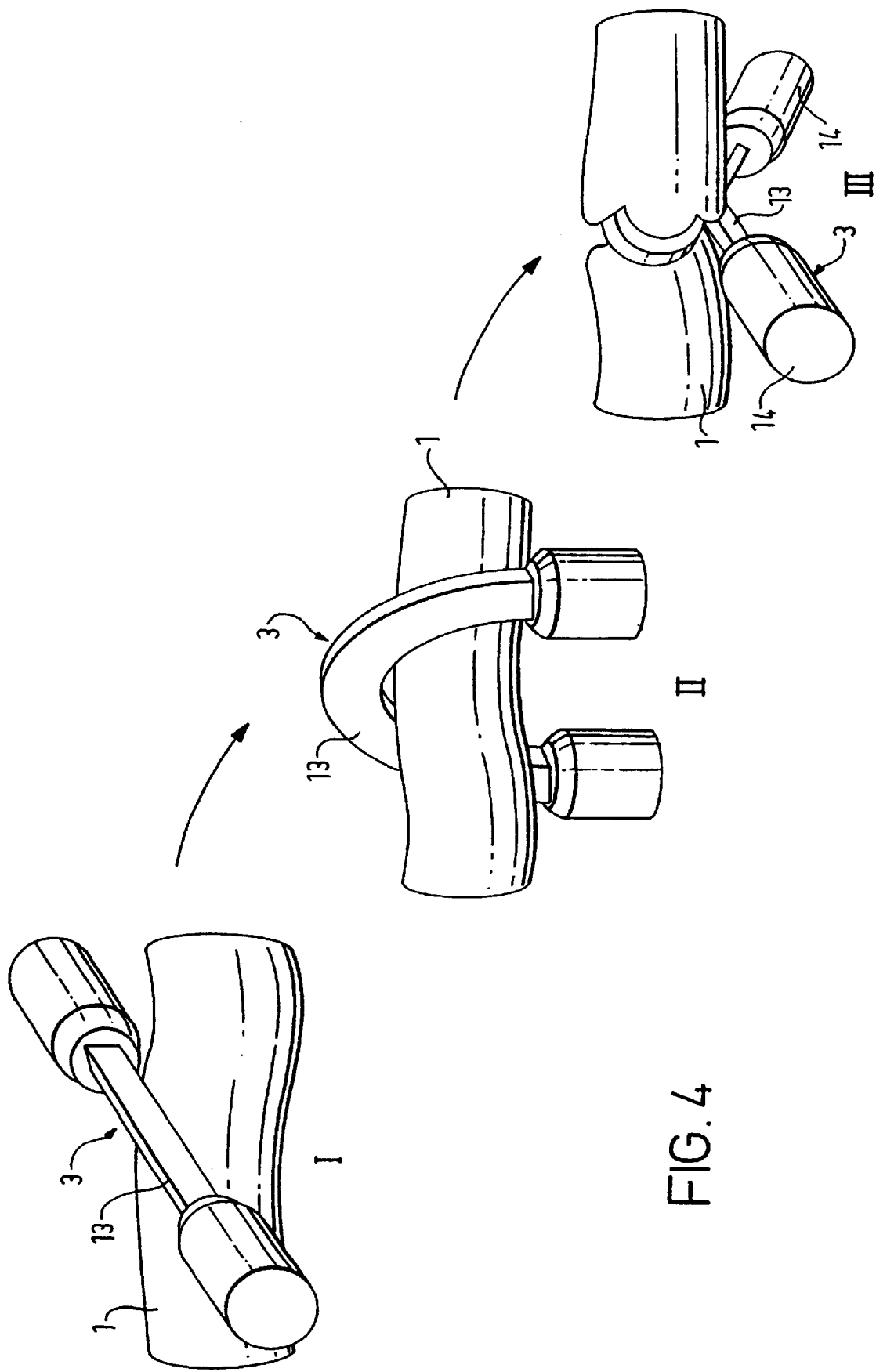
FIG. 4 shows the process of occlusion of a body passageway by the clip after expulsion from the device of FIG. 1.

The "memorised" shape of the clip is a tightly wound helix or spiral, as shown in FIGS. 3 and 4, and the material of the clip is such that the clip moves rapidly into that configuration in response to the temperature rise which is associated with release from the apparatus into an operating zone within a patient's body. The inner diameter of the spiral can be predetermined by adjusting the length of the elongate element 13. In addition, the torsional force applied to the body passageway 1 can be altered by adjusting the thickness of the elongate element 13 and by altering the physical state of the material at the time of initial deformation. These modifications are routine for those of ordinary skill in the art of resilient (e.g. "shape memory") materials.

Alternatively, the clips may be formed of an elastomeric material which is stored in a stretched form in the apparatus, and reverts to a pre-formed generally helical resting condition upon release from the apparatus, under the influence of the elastic restoring force.

FIG. 4 shows the stages in the application of a haemostatic clip 3 across a body passageway (in this case a vein). In Stage I the open haemostatic clip 3 is positioned across the vein. Upon release from the apparatus the haemostatic clip 3 begins to move to its generally helical shape (Stage II), In Stage III the haemostatic clip 3 wraps around the vein, occluding the lumen.

The clip is stored in a straight configuration within the shaft 2 of the apparatus (FIG. 1), and is urged along, the shaft in that configuration.

Referring now particularly to FIGS. 1 and 5 to 10, the apparatus will be described in more detail. The apparatus comprises three main sections; the handle 10, with trigger mechanism; a main body 14, having a casing wall and containing as clip control means a proximal ratchet release system 15 for the spring biassing the pressor rod 8, and a sprung cam mechanism 16 for opening and closing the port 6; and lastly the shaft 2, which comprises an outer shaft 2a, an inner hollow shaft 2b providing the cover member control means (the inner shaft 2b being proximally connected to the sprung cam 16 of the body 14), and the central pressor rod 8.

The handle 10 is of the pencil type, as described generally in WO-97/42884, with a mid-point third finger—thumb pivot, and provision for both second and fourth finger control on the forward (right as illustrated) surface 18. On the section adjacent to the body 14 of the apparatus lies the trigger 9. This is depressed for release of a haemostatic clip 3 by opening of the port 6, whereby the end clip twists out of the shaft 2, with simultaneous release of the pressor effect of the central pressor rod 8. One haemostatic clip 3 is released when the trigger 9 is fully depressed and the mechanism then remains static until release of the trigger by the surgeon, whereupon the inner hollow shaft 2b rotates to a 90° opposed position, so closing the distal port 6. Trigger release also causes the spring biassing to be reapplied on the pressor rod 8, thereby causing the pressor rod 8 to move forward and resume its forward effect upon the remaining haemostatic clips 3 in the apparatus.

The body 14 houses the links from the trigger 9 to the ratchet release system 15 and the cam mechanism 16. The cam mechanism 16 comprises a lightweight face-plate or cam 19, having a central aperture which receives the inner shaft 2b whereby the cam 19 is fixedly mounted on the inner shaft 2b. The cam is sprung via two opposed wire springs 20, 21, attached to the body casing 22. A link rod 23 from the trigger 9 is attached to one corner 19a of the cam, and rotates the cam 90° back and forth. Owing to the lightweight nature of the cam and inner shaft and the balance spring effect, the whole mechanism flips back and forth upon respective actuation and release of the trigger 9.

The link rod 23 moves up and down in line with the long axis of the handle 10. Behind the trigger 9 within the handle there is a sliding hinged mechanism 23a with yokes 23b to restrain the link rod 23 in the horizontal direction, which translates the reciprocal horizontal action of the trigger into the reciprocal vertical up and down movement of the link rod 23. The trigger is sprung (not shown) and thereby has a natural tendency to resume the extended, non-depressed state upon release by the surgeon.

In the embodiment shown, the shaft 2 is permanently closed over its distal end face 24 and fashioned from lightweight material, which is biologically inert, such as stainless steel. The outer 2a and inner 2b shafts are each provided with a side opening near the distal end thereof, forming the port 6 of the shaft. The opening of the outer shaft 2a is generally in line with the handle 10, i.e. on the under side of the shaft of the apparatus as illustrated in FIG. 1. The inner shaft 2b is rotatable within the outer shaft, as previously described, and the arrangement is such that the opening of the inner shaft can be aligned with the opening of the outer shaft to open the port 6 formed by the aligned openings. When the inner shaft 2b is rotated to the release, or 'open' position (FIG. 5) the two openings lie coincidental, providing an unhindered release for a haemostatic clip 3 through the port 6.

Figure 5:
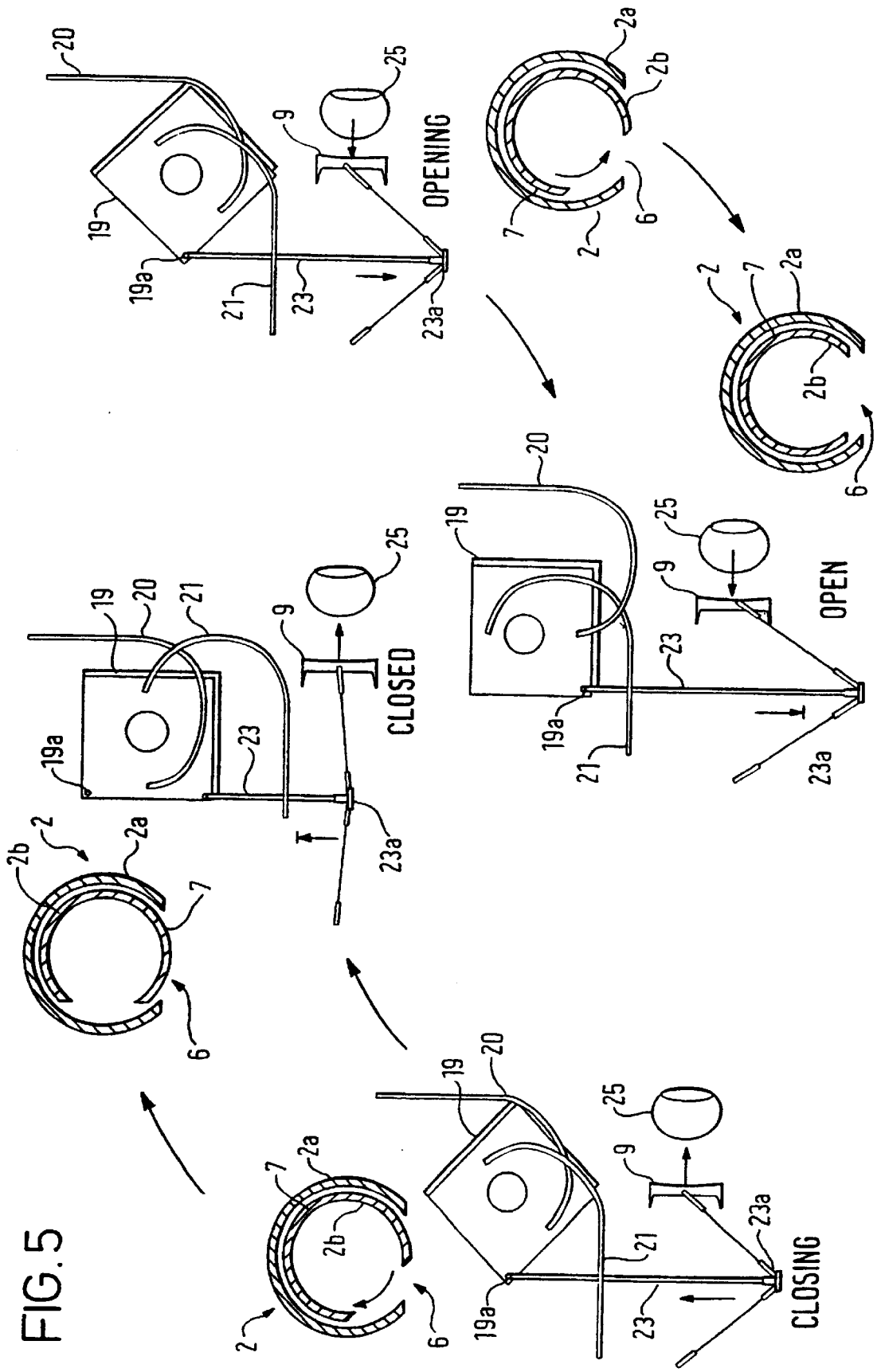
FIG. 5 shows schematically in transverse cross-section on the line V—V of FIG. 1 the synchronisation of the closure and clip drive means of the apparatus of FIG. 1.

FIG. 5 shows a functional schematic diagram of this process. It shows the 'opening' process upon actuation of the trigger by a surgeon's finger 25 and the 'closing' process upon release of the trigger 9. These states ("open" and "closed") refer to the condition of the port 6. With finger pressure (arrow A) the trigger 9 moves to the left as illustrated (is depressed), the two arms of the hinged mechanism move closer together within the handle 10 and thereby force the sliding mechanism down, away from the body 14 of the apparatus, so pulling the link rod 23 down, further along the handle 10. This rotates the cam 19 around, and thereby rotates the inner shaft 2b, this rotation being against the restoring force of the opposed wire springs 20, 21. The cam 19 is square in shape and rotates, sliding as it does so against the inner wall of the body casing, which is suitably of plastic. Once it begins to rotate it assumes an unstable position and can either flip back to the stable rest position (if the surgeon inadvertently, or purposefully prematurely releases the trigger before completion of the cycle). With continued finger pressure on the trigger, however, the cam 19 springs around to the next stable position (full length side of the cam 19 against the inner casing wall), which is reached with full depression of the trigger 9. At this point the inner shaft has moved through 90°, and the two distal openings lie coincidental. The port 6 is thus open and a clip can be released by its inherent tendency to twist out of the shaft.

Upon release of the finger pressure on the trigger 9, the hinged arms move apart, the link rod 23 moves up and the cam 19 rotates in the reverse direction. The sprung cam 19 moves around until it reaches the original stable position, the port 6 closes and the trigger 9 moves back to the neutral position.

The mechanism for temporary release of the spring biassing the pressor rod 8, in synchrony with the opening of the port 6, will now be described with particular reference to FIGS. 1 and 6 to 10.

Figure 6:
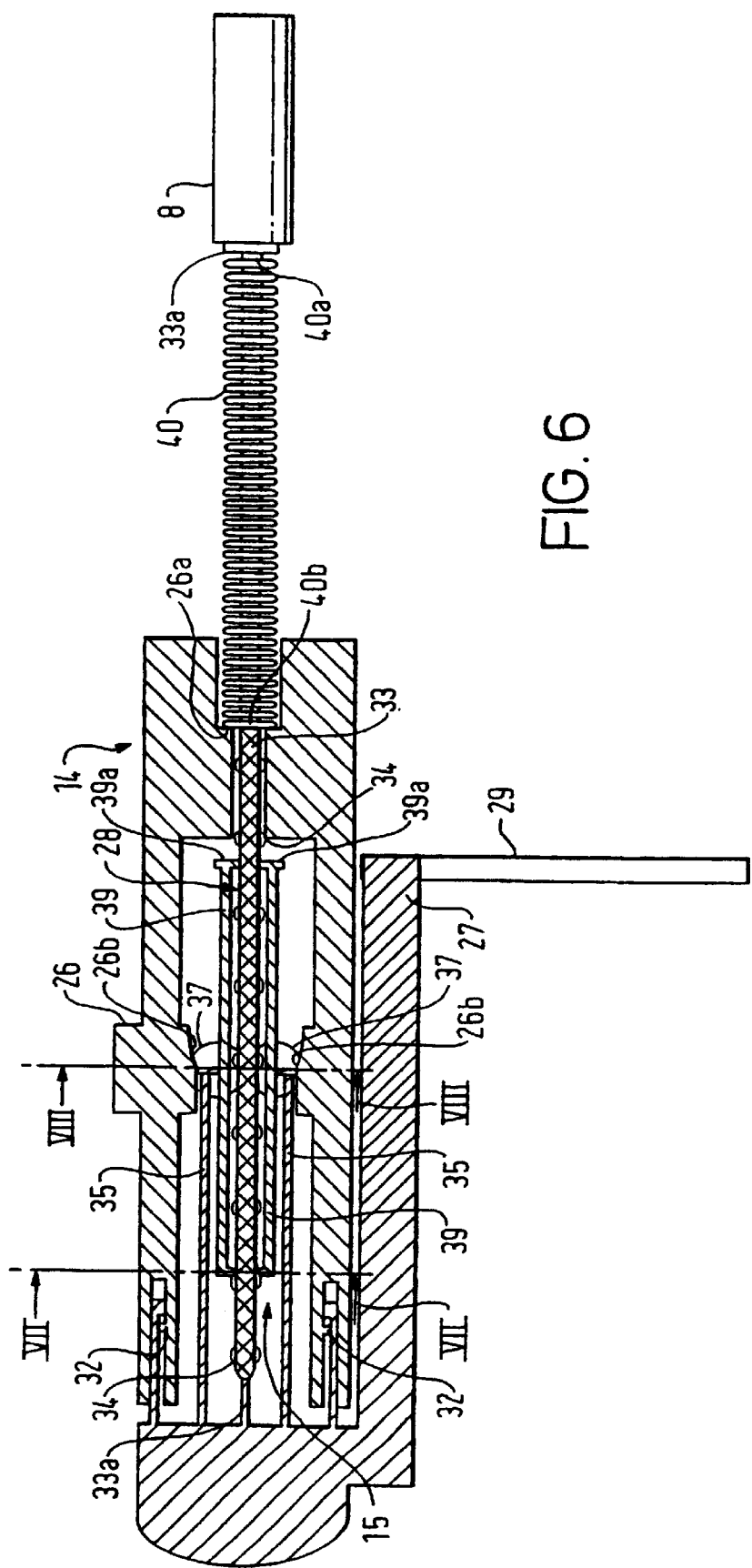
FIG. 6 shows an enlarged vertical cross-section of part of the apparatus of FIG. 1, showing part of the clip drive means in more detail.
Figure 7:
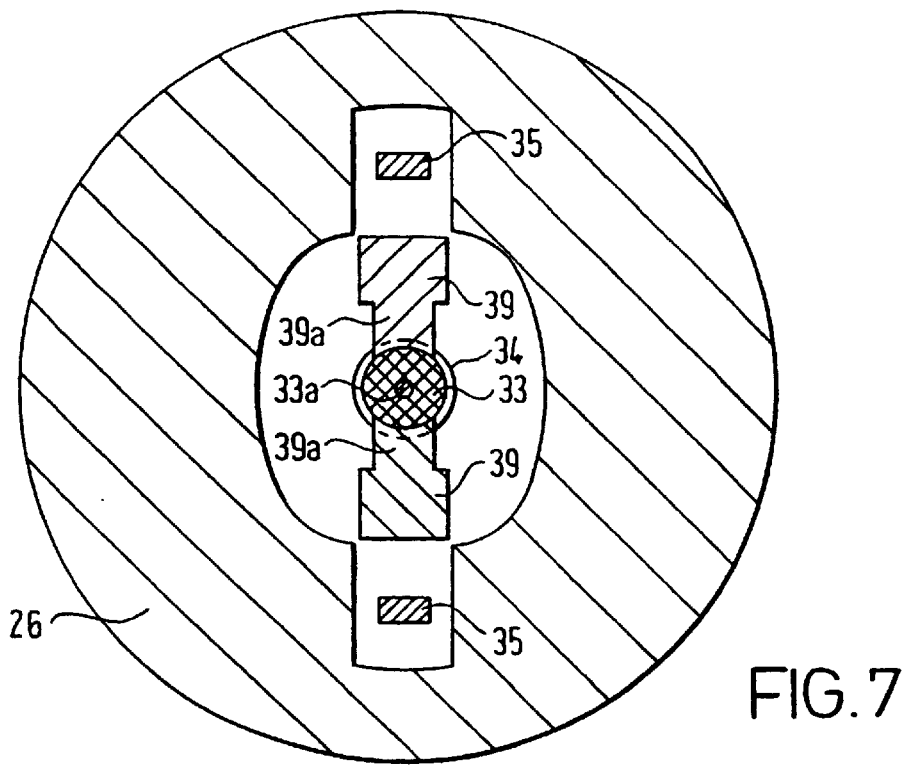
FIG. 7 shows an enlarged cross-sectional view along the line VII—VII of FIG. 6, looking in the direction of the arrows.
Figure 8:
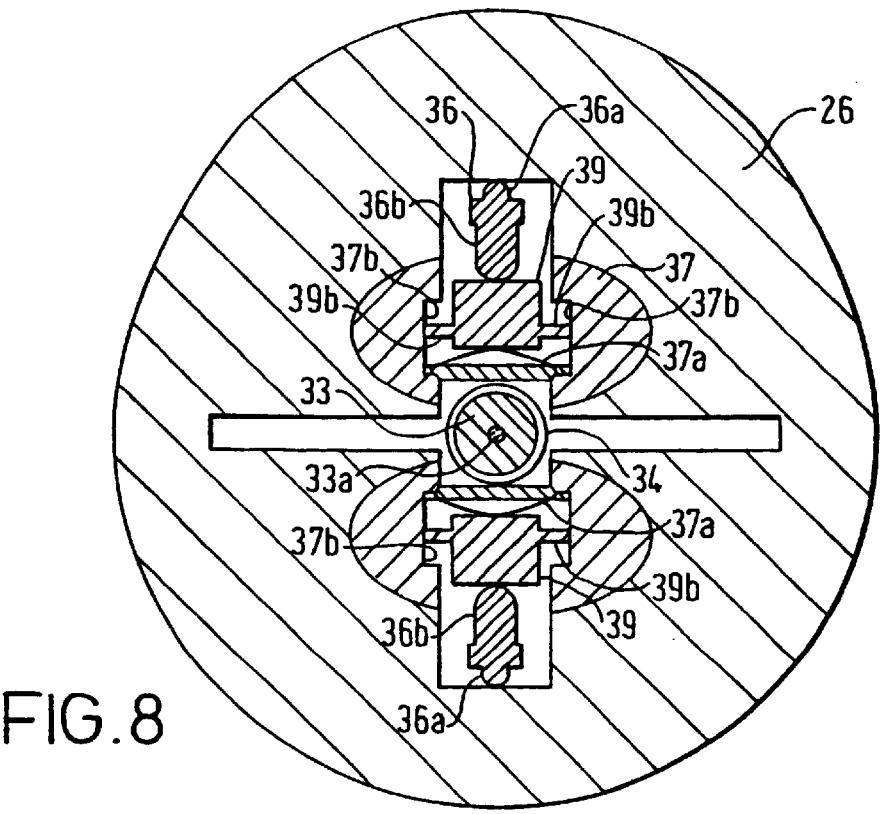
FIG. 8 shows an enlarged cross-sectional view along the line VIII—VIII of FIG. 6, looking in the direction of the arrows.
Figure 15A:
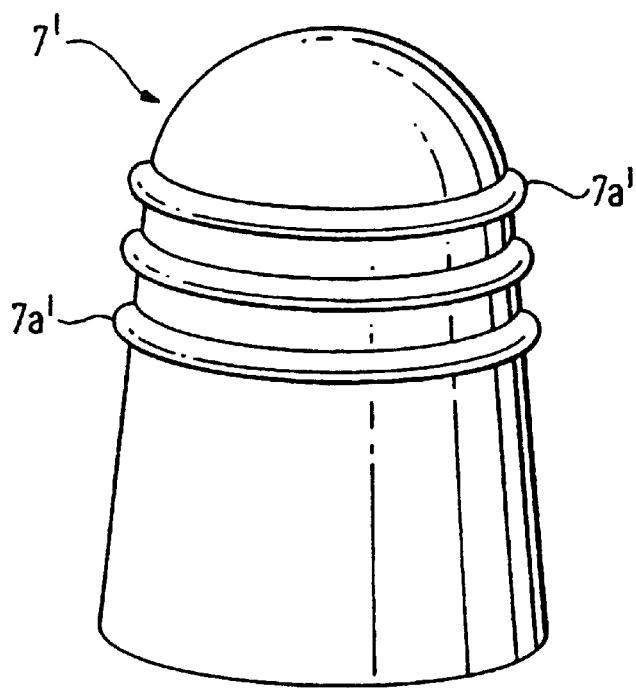
FIG. 15a shows a perspective detail of an alternative distal end cover for use with the apparatus of FIGS. 12 to 14.
Figure 15B:
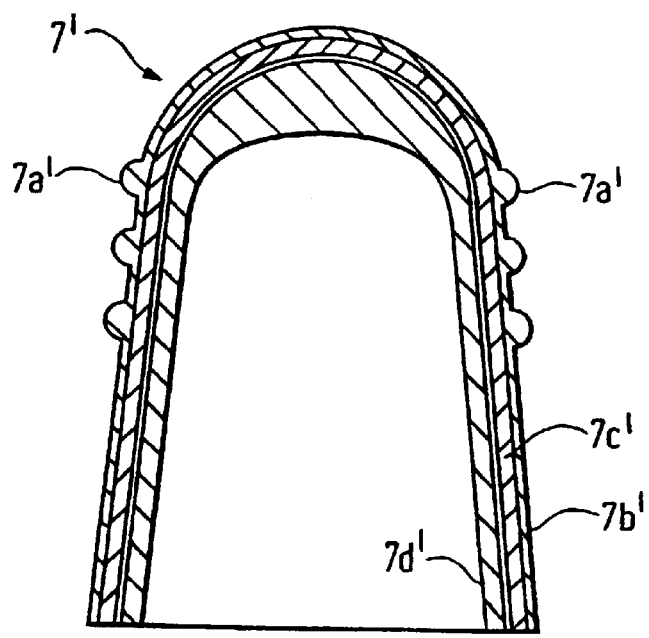

FIG. 6 shows a median partial longitudinal section of the proximal ratchet mechanism, housed within the body 14 casing. This mechanism controls the releasable spring biassing of the pressor rod 8 in synchrony with the opening and closing of the port 6. The mechanism comprises three main parts: a fixed hollow central casing part 26, which is mounted to the body 14 casing; a slidable part 27 which moves to and fro relative to the central casing part 26; and a ratchet part 28 within the central casing part 26.

The slidable part 27 is operatively linked to the trigger 9 by means of tracker rods 29, 30, 31 (see also FIG. 1) which transfer the horizontal movement of the trigger directly into horizontal movement of the slidable part 27. Trigger springs (not shown) are associated with the tracker rods 30,31, which urge the trigger and thereby the slidable part 27 into the resting (non-depressed) condition as shown in FIG. 1. The slidable part 27 is limited in its movement with respect to the central casing part 26 by stops 32.

The ratchet part 28 includes: a central ratchet rod 33 slidably mounted coaxially upon a central ratchet rod guide pin 33a which extends from the slidable part 27 along a significant portion of the length of the ratchet rod, internally of the ratchet rod 33; circumferential ratchet teeth 34 provided at intervals along the ratchet rod 33 in such a number and spacing that the ratchet mechanism will engage and function at generally the beginning of each trigger depression action; a pair of opposed releasable longitudinal ratchet gears 39 disposed over the ratchet rod 33 and having concave terminal teeth 39a which can overlie the circumference of the ratchet rod 33 and engage with the teeth 34 of the ratchet rod 33 when the ratchet gears are brought into engagement with the ratchet rod 33; a pair of transverse supports 37 extending across the central space of the casing part 26 on opposed sides of the ratchet rod 33 and each serving to support the respective ratchet gear 39 in an outwardly resiliently biassed manner by means of an intermediate arched leaf spring 37a mounted to the transverse support and further to slidingly guide the respective ratchet gear in its transverse to and fro movement into and out of engagement with the ratchet rod 33 via cooperating guide channels 37b of the transverse supports 37 and lateral projections 39b of the ratchet gears; (the guide channels 37b of each transverse support 37 being in the form of mutually inwardly directed vertical slots along each of which the respective lateral projection 39b of the ratchet gear can slide to and fro—i.e. towards and away from the ratchet rod correspondingly to the movement of the ratchet gear—and the lateral projections 39b being smaller than the width of the guide channels 37b so that pivotal movement of the ratchet gears is possible via the sliding pivot arrangement provided by each guide channel 37b and lateral projection 39b, while nevertheless the ratchet gear 39 is held captive by the guide channels 37b as far as longitudinal movement (i.e. to left or right as viewed in FIG. 6; respectively into or out of the paper as viewed in FIG. 8) is concerned); a pair of elongate resiliently bendable ratchet adjusters 35 mounted to the slidable part 27 and extending therefrom to overlie the ratchet gears 39 and each having a terminal T-head 36 providing one terminal projection 36a extending away from the respective ratchet gear and one terminal projection 36b extending towards the respective ratchet gear; and a pair of angled shoulders 26b provided on the interior wall of the casing 26 which cause a constriction between the casing wall and each ratchet gear 39 whereby the angled shoulder 26b of the casing wall can cooperate in a cam action with the projection 36a of each ratchet adjuster 36 when the ratchet adjuster 36 is drawn into the region of constriction (to the left as illustrated; see Arrows X in FIG. 9) in response to depression of the trigger, to force the ratchet gear into engagement with the ratchet rod, against the restoring force of the leaf springs 37a.

An advance spring 40 is held under compression and overlies the ratchet rod 33 between the distal end 33a of the ratchet rod 33, to which the distal end 40a of the spring is mounted, and a shoulder 26a of the casing part, against which the proximal end 40b of the spring bears. The restoring force of the advance spring thus urges the pressor rod 8 forward (to the right as illustrated; see Arrows Y in FIG. 10) when the ratchet and pressor rods are in contact.

Depression of the trigger 9 causes the slidable part 27 to move to the left as illustrated, relative to the central casing part 26, as far as the stops 32. This pulls the heads 36 of the ratchet adjusters 35 over the portions of the ratchet gears 39 which rest on the leaf springs 37a. The heads 36 are forced onto the ratchet gears by the constriction in the casing, against the restoring force of the leaf springs 37a. This forces the ratchet gears 39 to grip against the ratchet rod 33. The teeth 34 of the ratchet rod soon engage with the teeth 39a of the ratchet gears. Continued depression of the trigger 9 causes the slidable part 27 to pull the ratchet rod 33 to the left, to the point of full depression of the trigger (FIG. 9).

At the same time as the ratchet rod 33 is pulled to the left in association with the slidable part 27, the advance spring 40 is compressed. The pulling of the ratchet rod 33 out of contact with the pressor rod 8 releases the pressor effect on the haemostatic clips 3. At full depression of the trigger 9 a distal haemostatic clip is released from the apparatus, by the synchronised opening of the port 6. The remaining haemostatic clips 3 lie passively in line within the inner shaft 2b.

Upon release of the trigger 9, the port 6 closes and the trigger springs back to its resting condition. The slidable part 27 moves back (to the right) relative to the central casing part 26, and the heads 36 of the ratchet adjusters 35 move (to the right) out of the region of constriction of the casing wall (FIG. 10). Resilience of the ratchet adjusters 35 causes them to resume a parallel resting configuration out of contact with the ratchet gears 39. The pressure on the ratchet gears 39 is thus released and the ratchet gears 39 in turn lift off the central ratchet rod 33, under the restoring force of the leaf springs 37a. In turn, the ratchet adjusters 35 are splayed out of the way by the same restoring force (FIG. 10). The ratchet rod 33, being spring loaded by the advance spring 40, is thus released, rapidly advances forward within the inner shaft 2b, thereby re-exerting the pressor effect upon the haemostatic clips via the pressor rod 8. The line of clips then moves forward to take up the space vacated by the released clip, and the applicator is ready for the next application.

Referring now generally to FIGS. 12 to 21, an alternative surgical apparatus for occluding or encircling a body passageway comprises a housing in the general form of a hollow shaft 2' holding a line of surgical clips 3'. This alternative apparatus is designed for use in a relatively warm operating theatre environment.

The shaft 2' has a proximal end 4' and a distal end 5'. The distal end 5' of the shaft 2' is provided with a port 6' through which an individual clip 3' can be released. The port 6' is openable and closeable by means of a cover member 7' for the port, the cover member 7' being movable selectively to cover or uncover the port by manual operation. The cover member 7' takes the general form of a thermally insulated cup or thimble which can be manually push-fitted onto the distal end 5' of the shaft 2' to cover the port 6', and manually removed by a reverse procedure to uncover the port 6'. The cover member 7' may have external projections 7a', to enable the surgeon or his or her assistant to achieve a better grip on the cover member. The cover member 7' may suitably be formed of an insulating plastic such as ultra high density polyethylene or polyacetyl. The cup or thimble has two plastic layers, 7b', 7c', preferably further provided with a closely fitting inner liner 7d', also of plastic.

A drive member comprising a releasably spring-biassed pair of holding rails 8' of arcuate cross-section and in fixed mutual relationship are disposed within the shaft 2' and are slidable along the inner space of the shaft to urge the line of clips 3' held in contact with the rails 8', within the shaft to urge the line of clips 3' within the shaft towards the port 6'. The spring biassing is achieved by means of a return spring 8a' provided between the rails 8' and the proximal end 4' of the shaft 2', as shown in detail in FIG. 17. The return spring 8a' bears at one end against a pair of opposed spacer members 8b', fixed to the inner wall surface of the shaft 2' and adapted to space the internal parts from the wall of the shaft 2', and at the other end against a pair of spring stops 8c' which project radially outwards from the holding rails 8' (only one spring stop 8c' shown, in FIG. 17).

The apparatus includes a clip control device which controls the movement of the clips and the drive member within the shaft. More particularly, and as will be described in greater detail below, the clips 3' in the shaft are spaced apart via stops in the form of rounded projections on a central stator member, which is stationary with respect to longitudinal movement within the shaft but is transversely movable to and fro within the shaft under a spring bias. An orthogonal double synchronised cam device, spring loaded and actuable by external thumb or finger pressure from the surgeon, simultaneously retracts the stator member out of the plane of the line of clips so that the rounded stops do not impede advancement of the line of clips, advances the line of clips one clip-worth by urging of the holding rails 8' forward within the shaft 2' towards the distal end 5' 9 of the shaft, then restores the stator member back towards the plane of the line of clips so that the rounded stops impede reversal of the line of clips, and finally actuates the effect of the return spring 8a' on the holding rails 8' so that it moves back to its resting position in the shaft, sliding over the line of retained clips as it does so.

In this way, the movement of the clips in the shaft 2' and their individual expulsion from the port 6' of the shaft 2' can be controlled from the proximal end of the device by the surgeon. The clip control device is operable externally of the apparatus via a finger actuable trigger button 9' mounted on an ergonomically configured handle 10' for the apparatus. The handle 10' is provided with surface depressions 11', 12' whereby a surgeon can grip the handle.

Figure 16:
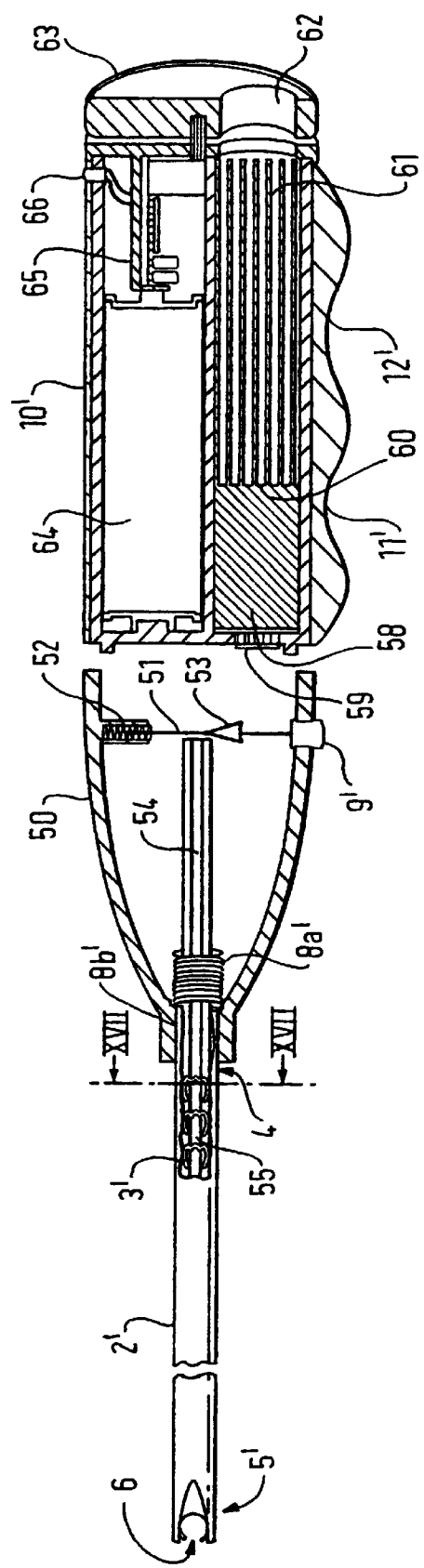
FIG. 16 shows a vertical longitudinal cross-sectional view of the apparatus of FIG. 12, showing the separation of the handle and housing parts.

As shown particularly in FIG. 16, the proximal end of the drive member and clip control device is housed within a hollow, generally conical, proximal part 50 of the housing, which is separable from the handle 10'. It is preferred that the housing, including the shaft 2', the generally conical proximal part 50, the internal mechanisms and parts and the loaded clips 3', will be supplied as a separate sterile unit which can be simply fitted (e.g. screwed or push-fitted) onto the reusable handle part. The sterile unit is not necessarily thrown away when the clips have been used, however. It may be taken apart, reloaded with clips and resterilised if desire, although this would have to be done in a workshop environment.

The clip control device will now be described in more detail, with particular reference to FIGS. 16 to 18.

The thumb-actuable button 9' is disposed at one end of a spindle rod 51 provided within the proximal housing part 50, the spindle rod being mounted at its other end to a compression spring 52 which spring biasses the button 9 and spindle rod 51 to the resting condition.

Figure 17:
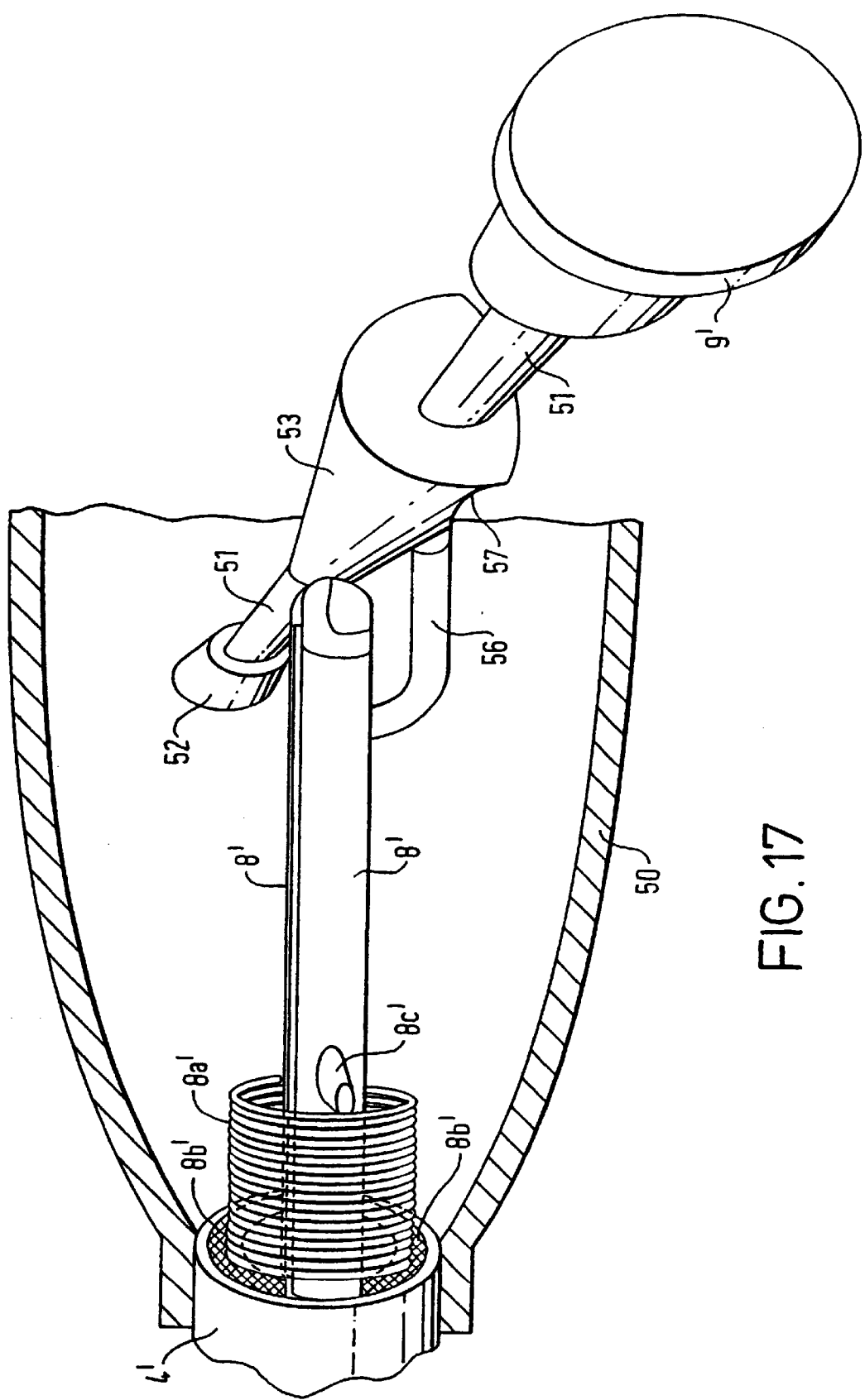
FIG. 17 shows a schematic perspective view of the proximal end of the housing part of the apparatus of FIGS. 12 to 16, to illustrate the drive member and clip control device.
Figure 18:
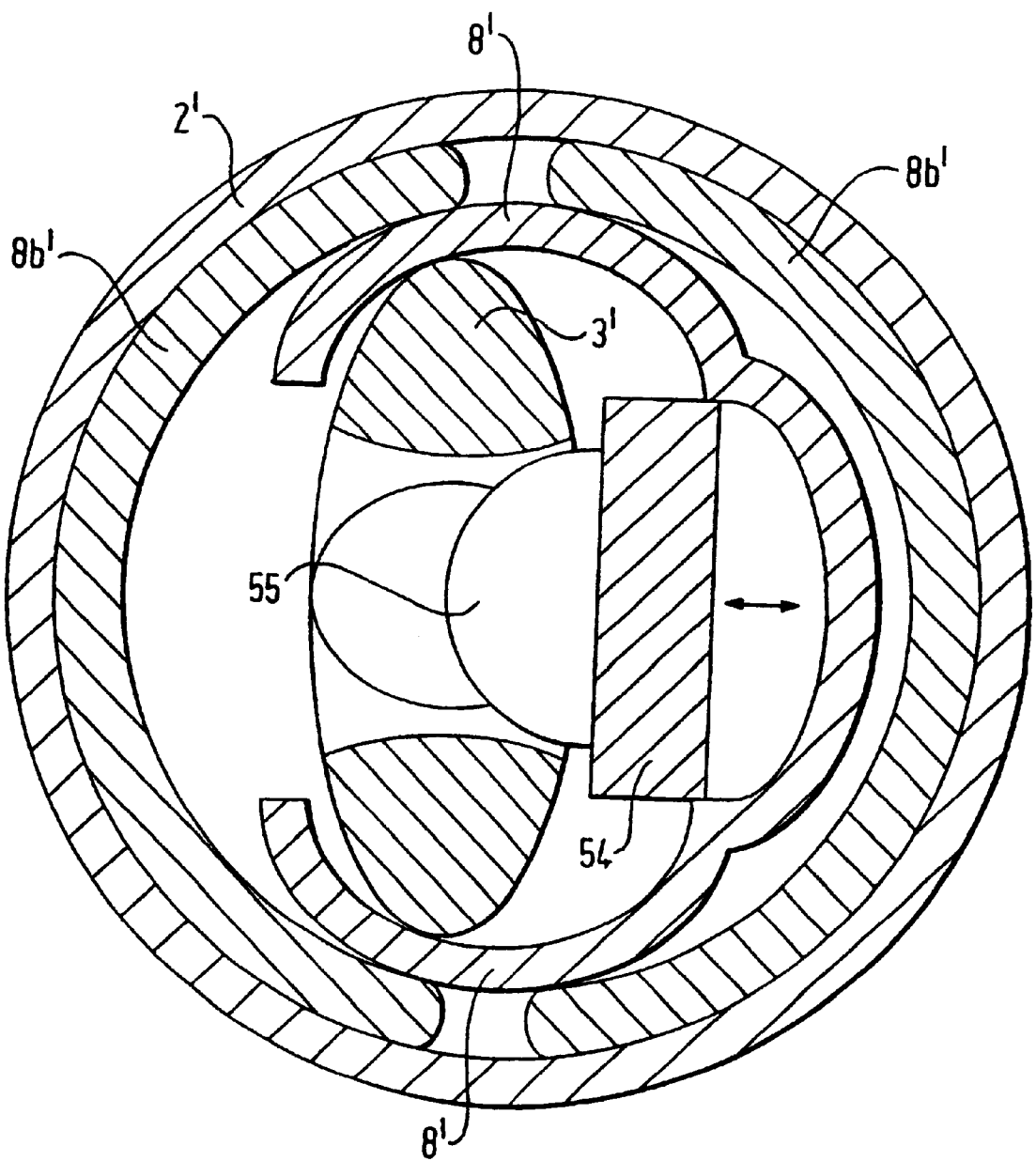
FIG. 18 shows a vertical cross-sectional view of the apparatus of FIG. 16, along the line XVIII—XVIII and looking in the direction of the arrows.

Generally centrally along the length of the spindle rod 51 there is provided the orthogonal double cam arrangement comprising a cone surface 53 scalloped on its underside (as viewed in FIGS. 16 and 17, FIG. 16 being considered as a top view and FIG. 17 being considered as a perspective view more from the side).

The cone surface 53 bears against the proximal end of the pair of holding rails 8' as the button 9' is depressed, urging the rails 8' into the shaft 2'. Because the rails 8' are holding the clips 3' between them (see FIG. 18), this will move the clips in the shaft 2' towards the distal port. Full depression of the button 9' will move the rails 8' and clips 3' by one clip increment, so introducing the distal clip 3' into the distal port 6' of the shaft.

The clips 3' are held in mutually spaced apart relation within the shaft by means of a stator member 54, which is located between the rails 8'. The stator member is stationary with respect to longitudinal movement within the shaft but is transversely movable to and fro within the shaft, as shown by the double-headed arrow in FIG. 18, under the biassing effect of spring 52. The stator member carries a series of spaced stops 55 along its length, the stops comprising rounded projections spaced one clip separation apart.

Extending from the proximal end of the stator member to its underside is a crooked finger projection 56 having an appropriately angled tip, which slides over the underside of the cone surface 53 as the cone surface moves when the button 9' is depressed. This secondary cam action causes the stator member 54 to retract from the plane of the clips sufficiently that the line of clips can be advanced in the shaft 2' by the primary cam action on the pair of rails 8' and the clips 3'. However, as soon as the scallop indentation 57 in the underside of the cone surface 53 is reached, the retraction of the stator member 54 stops.

On release of the button 9', springs 8a' and 52 release and act to return the mechanism to its resting condition. However, the synchronisation is such that the stops 55 of the stator member 54 move into the plane of the line of clips before that line of clips has been moved back by the rails 8'. Therefore, the stator member 54 catches the clips in their advanced state, and prevents them from moving back towards the proximal end of the shaft. Instead, the rails 8' merely slide back over the clips.

It is a feature of this apparatus that the clips are held in the shaft 2' at a relatively constant depressed temperature. This is achieved by providing a temperature control device in the handle 10'. The temperature control device serves to maintain the temperature of the parts of the shaft within the range of about 5 to 20° C., even when the instrument is being held by a surgeon or assistant, or is being used in a hot environment.

The temperature control device as illustrated is a Peltier effect thermal pump. The Peltier effect is a known cooling effect and Peltier effect heat pumps are marketed, e.g. by RS Components, P.O. Box 99, Corby, Northamptonshire, UK (telephone:+44 1536 201234). Any conventional Peltier device with a sufficient cooling effect can be used. In general terms, the Peltier effect, which was discovered in 1834 by Jean Peltier, relies on the phenomenon that the passage of an electric current through the junction of two dissimilar conductors can either heat or cool that junction, depending on the direction of the current. Heat generation/absorption rates are proportional to the magnitude of the current and the temperature of the junction. In commercial devices, semiconductors doped both p and n type typically form the elements of the couple and are soldered to copper connecting strips. Ceramic faceplates electrically insulate these connecting strips from external surfaces. A suitable semiconductor material is bismuth telluride.

Alternatively (not illustrated) a gas cooling device may be used, whereby the cooling effect of expansion of a pressurised gas (e.g. carbon dioxide) can be used to provide the necessary cooling, using the Joule-Thompson effect.

Thermostatic control (not shown) of the internal temperature of the apparatus may be provided, whereby the temperature can be maintained at a desired level.

In all cases, however, it is preferred that the cooling device be housed completely within the handle.

The cooling device is therefore a Peltier effect heat pump 58 which cools on its forward surface 59 (directed towards the interior of the housing) and pumps any heat gained towards the opposing surface 60. This surface 60 is in thermal contact with a metal heat sink 61, allowing the heat to be conducted away and lost to the atmosphere via a vent 62 in the end cover 63 of the handle. The end cover 63 is conveniently adapted as an on-off rotatable switch to acuate the cooling device, the vent 62 being open in the "on" position as shown in FIG. 16. A high current battery 64 is also contained Within the handle, and the outer casing of the handle is suitable made thermally and electrically insulating. The battery 64 is connected to a conventional electronic circuit board 65 provided with electrical components which reduce the relatively high voltage from the battery and provide a suitable current. A light emitting diode (LED) 66, indicates when the device is "on".

The internal mechanism of the housing is suitable formed predominantly of metal, for example stainless steel. In this way, the cooling effect of the heat pump in the handle is transferred efficiently to the clips. To maintain the apparatus as cool as possible, the terminal cover member 7' should be applied to the distal end of the shaft 2' whenever the apparatus is not in use. This prevents warm air from contacting the distal end clip of the apparatus. Alternatively or additionally, the shaft of the apparatus can be kept in an insulated or cooled holster when the apparatus is not in use.

The shaft itself and the proximal housing part 50 may most conveniently be made of a synthetic plastic such as ultrahigh molecular weight polyethylene or polyacetyl. This material is also convenient for the handle casing, since it provides excellent thermal/electrical insulation and structural durability. It is also suitable biologically, and has a non-slip surface.

The shaft 2' is designed to afford maximum external thermal insulation to the clips until final release. The distal end 5' is therefore shaped to afford the surgeon the convenience of pre-positioning the U-shaped mouth 6' across a vessel or duct, before trigger release. Trigger release does not propel the clip out of the end, but rather simply moves it into the U shaped terminal mouth 6' of the shaft, where it can be warmed by the anatomical structure. The clip is not mechanically deformed by the action of the trigger. This enables the release mechanism to be a simple light-touch button and not a conventional trigger shaped to provide mechanical leverage, which is traditionally necessary to crush and deform conventional clips.

Should a surgeon accidentally misplace a clip, a cooled probe can be applied to the clip to return the clip to its first (open) configuration, after which it can be removed and a fresh clip reapplied using the apparatus. Alternatively, the clip can be snipped or cut, so that it will fall away from the body passageway.

The apparatus may be provided with a clip counting device or an indicator device, to alert the surgeon when the supply of clips is becoming exhausted. A simple indicator would, for example, be a transparent window towards the distal end of the shaft, whereby the surgeon or his or her assistant can see when the supply of clips is about to be exhausted.

Figure 20:
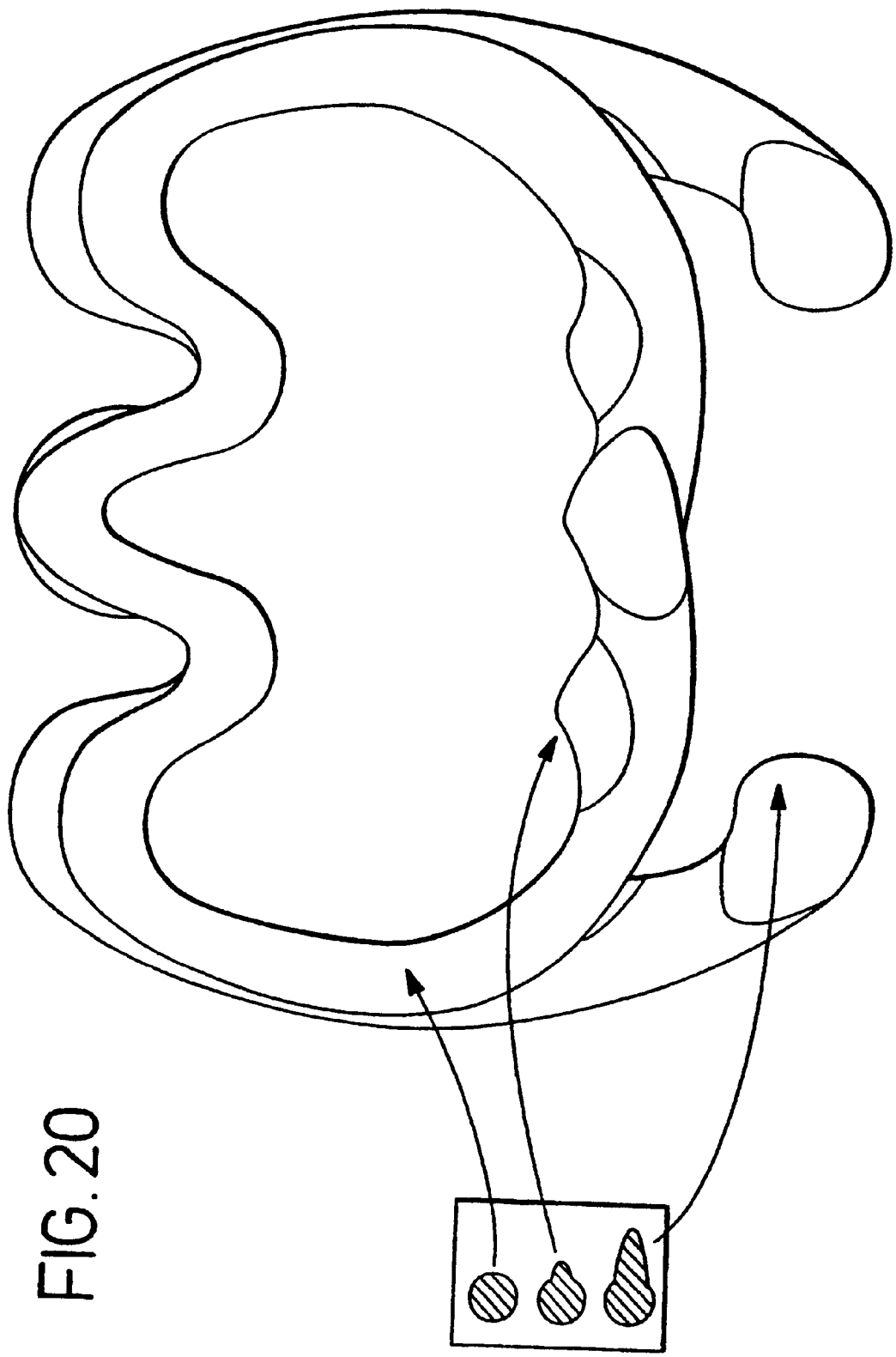
FIG. 20 shows the two configurations (a) and (b) from FIG. 19 in overlain relationship, to illustrate the deformation changes that the clip undergoes, and showing in the small insert box details of the cross-sectional configurations at various points.

Referring particularly to FIGS. 19 to 21, the preferred clip construction will now be described in detail.

In the first (low temperature) configuration the clip 3' is in the general form of a staple, having a convoluted central portion 70 in the form of a sinuous curve. The clip is formed of circular cross section Nitinol wire.

The central portion 70 has two legs 71, 72 extending therefrom in generally the same direction.

The convolutions of the central portion provide two apices 73, 74 directed towards the legs 71, 72 respectively. These apices provide shoulders against which the closing force of the legs in the second (body temperature) configuration can urge the body passageway.

As shown in FIG. 20, for example, the convoluted central portion of the clip has the desirable property that it permits the central portion of the clip to flatten at least the outer curves in the second configuration (see FIG. 20), so allowing the legs 71, 72 to clasp inwards towards the central portion of the clip with a good angular presentation and therefore good mechanical advantage. This deformation is illustrated by conside ring the changes to angles α and β as shown in FIG. 19, as the clip moves from its first (a) to its second (b) configuration. As shown in FIG. 19, angle α closes from about 59° to about 57°, whereas angle β opens from about 13° to about 53°.

The legs turn slightly mutually inwards and at their tips they are each provided with a wedge surface 75 which terminates to a wedge apex 76 at the end of the respective leg.

A little way along each leg 71, 72 there is provided an inwardly directed nip-head projection 77, of generally somewhat rounded profile (see the profiles in FIG. 20). This nip-head projection is arranged to bear towards one of the inwardly directed apices 73, 74 of the convoluted central portion of the clip in the second configuration of the clip, to maximise the pinching effect of the closure of the legs towards the central portion in the said second configuration.

It is preferred that in the second configuration of the clip (see FIG. 19(*b*)) the ends of the legs overlap. The degree of overlap shown in FIG. 19(*b*), for example, is sufficient to constitute "generally helical winding" within the terms of this patent. In achieving this overlap, the wedge surfaces 75 slide across each other. For this purpose, the wedge apices 76 are slightly offset from one another in the first configuration of the clip (see FIG. 21), so that they will not meet each other precisely square-on during the closing movement.

In addition, as shown in FIGS. 19 and 20, the closing movement involves the ends of the legs moving towards the central portion, so that each nip head projection 77 of each leg urges the body passageway (not shown) towards a respective one of the inwardly directed apices 73, 74 of the central portion.

The end result is secure and highly effective constriction or encircling of the body passageway between the legs of the clip and the central portion.

The foregoing broadly describes the invention without limitation to particular embodiments thereof. Variations and modifications as will be readily apparent to those of ordinary skill in this art are intended to be included within the scope of this application and subsequent patent(s).

What is claimed is:

1. A surgical apparatus for occluding or encircling a body passageway, the apparatus comprising:
    (a) a housing holding at least one clip, wherein the at least one clip comprises an elongate element having first and second ends and an intermediate central portion, the at least one clip comprising a temperature-dependent shape memory material and is resiliently movable, wherein in response to a temperature increase from a first temperature to a second temperature, the at least one clip changes under an inherent biasing force from a first configuration in which the first and second ends of the at least one clip are spaced apart to allow the body passageway to pass therebetween, to a second configuration in which the at least one clip is deformed on itself so that the at least one clip grips or encircles the body passageway, wherein the at least one clip is held at the first temperature within the housing in the first configuration, wherein the housing has a port through which at least one clip can be released to occlude or encircle the body passageway;
    (b) a drive member disposed within the housing and movable therein to urge at least one clip within the housing towards the port thereof; and
    (c) a clip control device associated with the drive member and operable externally of the housing to control the movement of the at least one clip therein and expulsion of the at least one clip therefrom.

2. The apparatus of claim 1, further comprising:
    a cover member for the port of the housing, wherein the cover member is movable selectively to cover or uncover the port.

3. The apparatus of claim 1, further comprising:
    a temperature control device for maintaining the at least one clip at the first temperature within the housing.

4. The apparatus of claim 3, wherein the first temperature is from about 0° C. to about 25° C.

5. The apparatus of claim 4, wherein the first temperature is from about 5° C. to about 10° C.

6. The apparatus of claim 1, wherein the second temperature is about 37° C.

7. The apparatus of claim 1, wherein each of the at least one clip is aligned in the housing with the ends directed generally towards the port of the housing.

8. The apparatus of claim 7, wherein each of the at least one clip is connected together in a cartridge arrangement.

9. The apparatus of claim 1, wherein the at least one clip is held under substantially zero mechanical stress.

10. The apparatus of claim 1, further comprising:
    a guide member which slidably supports the at least one clip in a location whereby the drive member can urge the at least one clip towards the port of the housing.

11. The apparatus of claim 1, wherein the port of the housing is adapted to lie adjacent to the body passageway externally and to receive a clip internally, whereby the ends of the clip substantially overlie the body passageway and are free to move in response to heat transferred to the clip from the body passageway and any surrounding body tissues and fluids, the movement of the ends of the clip being a movement closing the clip around the body passageway.

12. The apparatus of claim 1, wherein the port of the housing is configured as a notch at a distal end of a hollow shaft, the notch being adapted to receive the body passageway externally and the clip internally.

13. The apparatus of claim 1, wherein the portion of the apparatus that is in contact with the at least one clips comprises a thermoconductive material, whereby body heat is conveyed to at least one clip immediately prior to expulsion thereof and is conveyed away from a remaining at least one clip when the apparatus is not in use.

14. The apparatus of claim 1, wherein the at least one clip is adapted so that in the second configuration thereof the at least one clip is generally helically wound on itself around the body passageway.

15. A surgical clip for occluding or encircling a body passageway, the clip comprising an elongate element having first and second ends and an intermediate central portion, the clip comprising a temperature-dependent shape memory material and being resiliently movable, wherein in response to a temperature increase from a first temperature to a second temperature, the clip changes under an inherent biassing force from a first configuration in which the first and second ends of the clip are spaced apart to allow the body passageway to pass, therebetween, to a second configuration in which the clip is deformed on itself so that the clip grips or encircles the body passageway, wherein the first and second ends of the clip are legs which in the first configuration of the clip extend in the same general direction as each other from the intermediate central portion, wherein the intermediate central portion has at least one apex directed generally towards the legs of the clip.

16. The surgical clip of claim 15, wherein the clip comprises a shape memory alloy.

17. The surgical clip of claim 16, wherein the alloy is Nitinol having an austenite finish temperature $A_f$ no greater than about 35° C.

18. The surgical clip of claim 17, wherein the Nitinol has an martensite start temperature $M_s$ which is at least 10° C. below $A_f$.

19. The surgical clip of claim 15, wherein the intermediate central portion of the clip has a zig-zag shape.

20. The surgical clip of claim 15, wherein the intermediate central portion of the clip has a sinuously curved shape.

21. The surgical clip of claim 15, wherein the intermediate central portion of the clip has at least two apices directed generally towards the legs of the clip.

22. The surgical clip of claim 15, wherein the legs of the clip are provided at their ends with mutually inwardly directed wedge surfaces, whereby the ends can slide over each other on closure of the clip.

23. The surgical clip of claim 15, wherein each leg of the clip is provided with an enlarged nip-head projection, inwardly directed relative to an apex of the central portion of the clip and arranged to bear towards the apex on closure of the clip.

24. The surgical clip of claim 15, wherein the first and second ends of the clip are legs which in the second configuration of the clip are turned inwardly toward the intermediate central portion of the clip, whereby the body passageway is gripped between the legs and the intermediate central portion of the clip, or encircled by the legs and the central portion of the clip, the intermediate central portion being convoluted in the second configuration.

25. The surgical clip of claim 15, wherein the first and second ends of the clip are adapted so that in moving from the first to the second configuration, the ends of the clip can slide over each other as the clip deforms into its second configuration.

26. The surgical clip of claim 15, wherein the first and second ends of the clip are legs which are provided with enlarged nip-head projections along their lengths, whereby in the second configuration of the clip, the projections nip the body passageway against the intermediate central portion of the clip.

27. The surgical clip of claim 15, wherein the first configuration of the clip is substantially rectilinear and the second configuration of the clip is generally helically wound on itself, whereby if the clip comprises an elastomeric material, the first configuration is achievable by holding the clip constrained in said rectilinear configuration against a resilient restoring force tending to move the clip into the second configuration thereof.

28. The surgical clip of claim 15, being of a dimension suitable for use in haemostasis.

29. The surgical clip of claim 15, being of a dimension suitable for use in ligation.

30. The surgical clip of claim 15, being of a dimension suitable for use in male or female sterilisation.

31. The surgical clip of claim 15, being of a dimension suitable for use in vascular occlusion.

32. The surgical clip of claim 15, being of a dimension suitable for use in cardiac occlusion.

33. The surgical clip of claim 15, being of a dimension suitable for use in the occlusion of body ducts prior to resection.

34. A surgical method for occluding or encircling a body passageway, comprising the steps of:
   (a) providing a clip comprising an elongate element having first and second ends and an intermediate central portion, the clip comprising a temperature dependent shape memory material and being resiliently movable, in response to an increase in temperature from a first temperature, substantially below body temperature, to body temperature under an inherent biassing force from first configuration, in which the ends are spaced apart to allow the body passageway to pass therebetween, to a second configuration in which the clip is deformed on itself so that the clip grips or encircles the body passageway, wherein the first and second ends are legs which in the first configuration extend in the same general direction as each other from the intermediate central portion, and the intermediate central portion has at least one apex directed generally towards the legs of the clip, the clip being provided at the first temperature and in the first configuration thereof;
   (b) offering the clip to the body passageway so that the body passageway is received substantially between the ends of the clip; and
   (c) allowing the temperature of the clip to rise to approach body temperature by the proximity of the body passageway to the clip, whereby the clip deforms into its second configuration around the body passageway.

35. The surgical method of claim 34, including the steps of:
   (a) utilizing a surgical apparatus having a housing for holding the clip, the housing having a port through which a clip can be released; and
   (b) offering the clip to the body passageway by locating the port of the surgical apparatus in proximity to the body passageway and expelling a clip through the port, whereby the clip resiliently deforms itself onto the body passageway.

* * * * *